United States Patent
Nakamura et al.

(10) Patent No.: US 10,421,760 B2
(45) Date of Patent: Sep. 24, 2019

(54) PYRROLO[2,3-D]PYRIMIDINE COMPOUND OR SALT THEREOF

(71) Applicant: TAIHO PHARMACEUTICAL CO., LTD., Chiyoda-ku (JP)

(72) Inventors: Masayuki Nakamura, Tsukuba (JP); Hiroyoshi Yamanaka, Moriya (JP); Morihiro Mitsuya, Tsukuba (JP); Takafumi Harada, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/746,208

(22) PCT Filed: Jul. 29, 2016

(86) PCT No.: PCT/JP2016/072258
§ 371 (c)(1),
(2) Date: Jan. 19, 2018

(87) PCT Pub. No.: WO2017/022648
PCT Pub. Date: Feb. 9, 2017

(65) Prior Publication Data
US 2018/0208598 A1 Jul. 26, 2018

(30) Foreign Application Priority Data

Jul. 31, 2015 (JP) .................. 2015-152123

(51) Int. Cl.

| | |
|---|---|
| *C07D 487/04* | (2006.01) |
| *A61K 31/519* | (2006.01) |
| *A61P 25/00* | (2006.01) |
| *A61K 47/32* | (2006.01) |
| *C07D 207/30* | (2006.01) |
| *C07D 307/34* | (2006.01) |
| *A61P 29/00* | (2006.01) |

(52) U.S. Cl.
CPC .......... *C07D 487/04* (2013.01); *A61K 31/519* (2013.01); *A61K 47/32* (2013.01); *A61P 25/00* (2018.01); *A61P 29/00* (2018.01); *C07D 207/30* (2013.01); *C07D 307/34* (2013.01)

(58) Field of Classification Search
CPC .................................................. C07D 487/04
See application file for complete search history.

(56) References Cited

U.S. PATENT DOCUMENTS

| | | | |
|---|---|---|---|
| 6,635,762 | B1 | 10/2003 | Blumenkopf et al. |
| 2004/0058922 | A1 | 3/2004 | Blumenkopf et al. |
| 2006/0183761 | A1 | 8/2006 | Ledeboer et al. |
| 2014/0171454 | A1 | 6/2014 | Ledeboer et al. |
| 2014/0349998 | A1 | 11/2014 | Ahearn et al. |
| 2015/0239900 | A1 | 8/2015 | Li et al. |
| 2016/0340353 | A1 | 11/2016 | Nakamura et al. |
| 2017/0119743 | A1 | 5/2017 | Nakamura et al. |

FOREIGN PATENT DOCUMENTS

| | | |
|---|---|---|
| JP | 2002-518394 A | 6/2002 |
| JP | 2008-528705 A | 7/2008 |
| WO | WO 99/65909 A1 | 12/1999 |
| WO | WO 2006/096270 A1 | 9/2006 |
| WO | WO 2013/085802 A1 | 6/2013 |
| WO | WO 2015/054572 A1 | 4/2015 |
| WO | WO 2015/119126 A1 | 8/2015 |

OTHER PUBLICATIONS

Furumoto. BioDrugs, 2013, 27(5), 431-38. (Year: 2013).*
"Multiple Sclerosis: Prevention", https://www.floridahospital.com/multiple-sclerosis-ms/prevention-multiple-sclerosis-ms, accessed Dec. 27, 2018. attached as pdf (Year: 2018).*
"Rheumatoid arthritis—prevention", http://www.webmd.com/rheumatoid-arthritis/tc/rheumatoid-arthritis-prevention, accessed Aug. 28, 2009, attached as pdf (Year: 2009).*
International Search Report dated Oct. 4, 2016 in PCT/JP2016/072258 filed Jul. 29, 2016.
Mark E. Flanagan, et al., "Discovery of CP-690,550: A Potent and Selective Janus Kinase (JAK) Inhibitor for the Treatment of Autoimmune Diseases and Organ Transplant Rejection," Journal of Medicinal Chemistry, vol. 53, No. 24, 2010, pp. 8468-8484.
Kamran Ghoreschi, et al., "Janus kinases in immune cell signaling," Immunological Reviews, vol. 228, 2009, pp. 273-287.
Melanie G. Cornejo, et al., "JAK3: A two-faced player in hematological disorders," The International Journal of Biochemistry & Cell Biology, vol. 41, 2009, pp. 2376-2379.

(Continued)

*Primary Examiner* — Noble E Jarrell
(74) *Attorney, Agent, or Firm* — Oblon, McClelland, Maier & Neustadt, L.L.P.

(57) ABSTRACT

Provided are a novel compound or a salt thereof, and a pharmaceutical composition comprising the same, which selectively and strongly inhibit JAK3, exhibit an excellent activity for suppressing the growth of human peripheral blood monocytes and an excellent oral absorbability, and exhibits an activity of inhibiting IL-2-induced IFN-γ production in vivo. A compound represented by formula (I) [wherein X represents —CH=CH—, —NH—, a sulfur atom or an oxygen atom; and n represents an integer of 0 to 2], or a salt thereof.

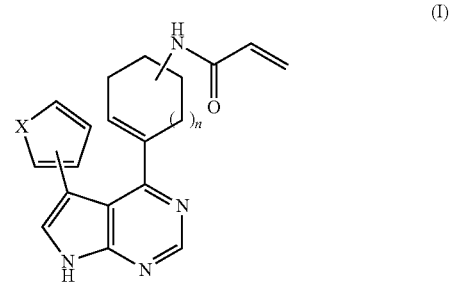

(I)

8 Claims, 2 Drawing Sheets

(56) References Cited

OTHER PUBLICATIONS

Anastassios C. Papageorgiou, et al., "Is JAK3 a new drug target for immunomodulation-based therapies?" TRENDS in Pharmacological Sciences, vol. 25, No. 11, Nov. 2004, pp. 558-562.

Seiji Yokoyama, et al., "Tofacitinib, a janus kinase inhibitor demonstrates efficacy in an IL-15 transgenic mouse model that recapitulates pathologic manifestations of celiac disease," J. Clin. Immunol., vol. 33, No. 3, Apr. 2013, 14 Pages.

Wei Xu, et al., "Hemagglutinin from the H5N1 Virus Activates Janus Kinase 3 to Dysregulate Innate Immunity," PLoS ONE, e31721, vol. 7, No. 2, Feb. 2012, pp. 1-11.

Ghee Chong Koo, et al., "*Janus Kinase* 3-Activating Mutations Identified in Natural Killer/T-cell Lymphoma," Cancer Discovery, vol. 2, Jul. 2012, 8 Pages.

\* cited by examiner

[Figure 1]
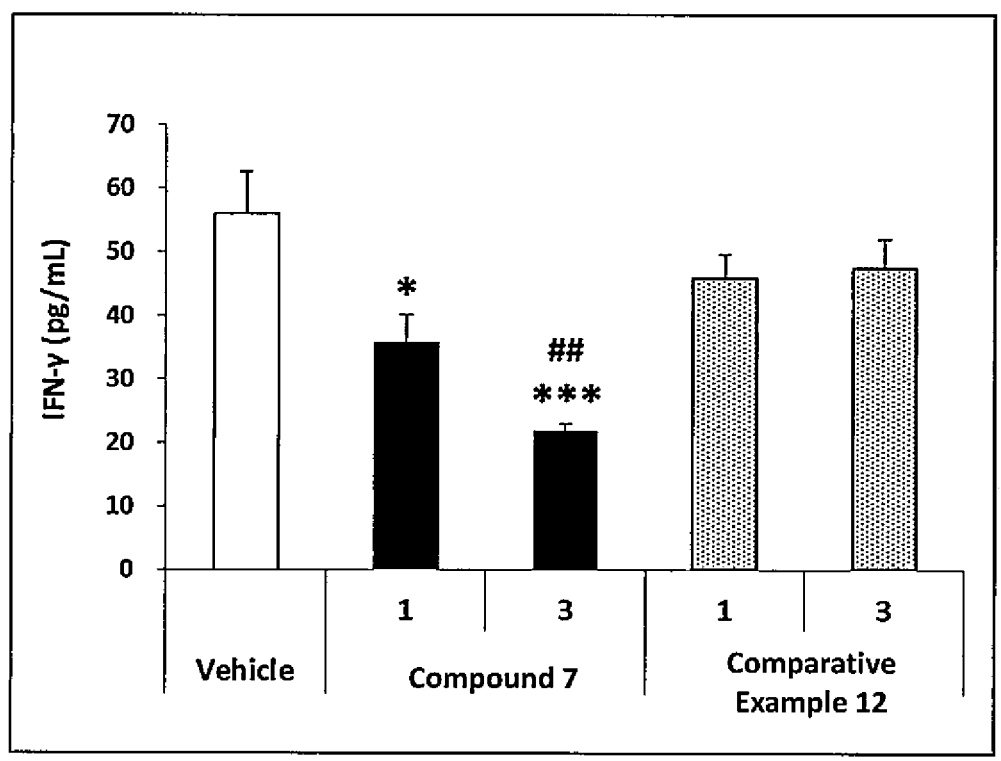

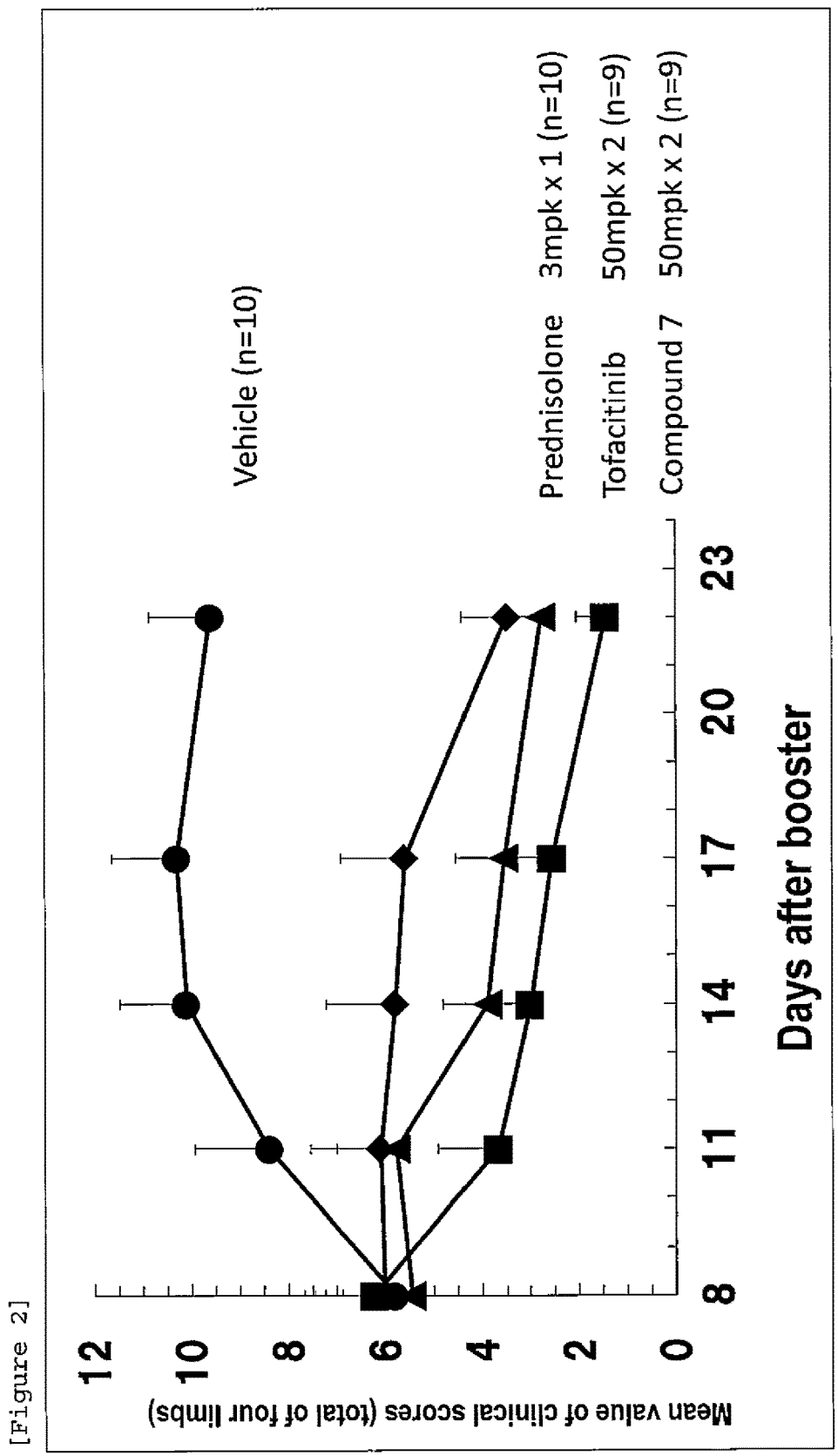

US 10,421,760 B2

PYRROLO[2,3-D]PYRIMIDINE COMPOUND OR SALT THEREOF

FIELD OF THE INVENTION

The present invention relates to a novel pyrrolo[2,3-d]pyrimidine compound or a salt thereof having a selective JAK3-inhibiting action and a pharmaceutical composition comprising a pyrrolo[2,3-d]pyrimidine compound or a salt thereof as an active ingredient.

BACKGROUND OF THE INVENTION

It has been known that JAK3, as well as JAK1, JAK2 and TYK2, is a non-receptor tyrosine kinase belonging to a JAK family, and that JAK3 is involved in the signaling of various cytokines.

JAK1, JAK2 and TYK2 are expressed in a wide range of tissues, whereas the expression of JAK3 is mainly limited to lymphocytes such as T cells, B cells, and natural killer cells. JAK1- and JAK2-deficient mice are embryonic lethal, or die soon after they are born. On the other hand, JAK3-deficient mice or humans develop severe combined immunodeficiency due to the dysfunction of lymphocytes.

It is assumed that a JAK3 inhibitor will inhibit the signals of six types of cytokines (i.e., IL-2, IL-4, IL-7, IL-9, IL-15, and IL-21), so as to specifically suppress the function of lymphocytes such as T cells or B cells, which play an important role in an immune system. Thus, such a JAK3 inhibitor is expected to be an effective therapeutic agent for diseases associated with activation of the aforementioned cells, having minimum expression of side effects (Non Patent Documents 1 and 2).

It has been reported that examples of the disease, which can be treated with the JAK3 inhibitor, include autoimmune disease (rheumatoid arthritis, multiple sclerosis, systemic lupus erythematosus, scleroderma, polymyositis-dermatomyositis, Sjogren's syndrome, Behcet's disease, etc.), allergic disease (bronchial asthma, allergic rhinitis/hay fever, atopic dermatitis, food allergy, anaphylaxis, drug allergy, hives, conjunctivitis, etc.), nervous system disease (multiple sclerosis, Alzheimer's disease, etc.), inflammatory bowel disease (ulcerative colitis, Crohn's disease), psoriasis, contact dermatitis, diabetes, celiac disease, viral infectious disease, acute respiratory distress syndrome (ARDS), graft-versus-host disease (GVHD), transplant rejection, hematologic malignancy (lymphoma, leukemia), and other malignant tumors (Non Patent Documents 3 to 6).

Clinically, Tofacitinib (Pfizer), which is a JAK3 inhibitor, has been used as a therapeutic agent for rheumatoid arthritis. However, it has been reported that Tofacitinib has low selectivity to JAK3, and thus that this agent has side effects (lipid increase, anemia, neutropenia, immunosuppression, etc.), which are caused by the inhibition of JAK1 and JAK2 by the agent (Non Patent Document 7).

Moreover, it has been reported so far that a pyrrolopyrimidine compound having a cyclic substituent at position 4 (Patent Document 1), a pyrrolopyrimidine compound having cyclohexene at position 4 (Patent Document 2), and a pyrrolopyrimidine compound having an aromatic group substituted with acrylamide at position 4 (Patent Document 3) exhibit JAK-inhibiting activity.

CITATION LIST

Patent Document

[Patent Document 1] US Publication No. 20040058922
[Patent Document 2] International Publication No. WO 2006/096270
[Patent Document 3] International Publication No. WO 2013/085802
[Patent Document 4] International Publication No. WO 2015/054572

Non Patent Document

[Non Patent Document 1] Immunol Rev., 2009, vol. 228 (1), p. 273-287
[Non Patent Document 2] Int J Biochem Cell Biol., 2009, vol. 41 (12), p. 2376-2379
[Non Patent Document 3] Trends Pharmacol Sci., 2004, vol. 25 (11), p. 558-562
[Non Patent Document 4] J Clin Immunol., 2013, vol. 33 (3), p. 586-594
[Non Patent Document 5] PLoS One., 2012, vol. 7 (2), e31721
[Non Patent Document 6] Cancer Discov., 2012, vol. 2 (7), p. 591-597
[Non Patent Document 7] J Med Chem., 2010, vol. 53 (24), p. 8468-8484

SUMMARY OF THE INVENTION

Problem to be Solved by the Invention

However, with regard to the compound described in Patent Document 1, a nitrogen atom directly binds to position 4 of a pyrrolo[2,3-d]pyrimidine compound, and Patent Document 1 does not describe a cycloalkenyl group substituted with acrylamide at position 4. Moreover, with regard to the compound described in Patent Document 2, this publication does not describe an acrylamide-substituted cycloalkenyl group at position 4 of a pyrrolo[2,3-d]pyrimidine compound. Furthermore, the compound described in Patent Document 2 has low selectivity to JAK3, and also, its inhibitory activity is not sufficient. Further, Patent Document 3 does not describe a pyrrolo[2,3-d]pyrimidine compound, to position 4 of which an acrylamide-substituted cycloalkenyl group binds.

On the other hand, a pyrrolo[2,3-d]pyrimidine compound having piperazine at position 4 has been reported as a KRAS inhibitor having a G12C mutation (Patent Document 4). However, Patent Document 4 does not describe inhibitory activity on JAK3.

Therefore, it is an object of the present invention to provide a novel compound, which selectively and strongly inhibits JAK3, exhibits an excellent activity for suppressing the growth of human peripheral blood monocytes (hereinafter referred to as "PBMC") and an excellent oral absorbability, and exhibits an activity of inhibiting IL-2-induced IFN-γ production in vivo, or a salt thereof, and a pharmaceutical composition comprising the same.

Means for Solving the Problem

As a result of intensive studies directed towards achieving the aforementioned object, the present inventors have found that a group of compounds comprising pyrrolo[2,3-d]pyrimidine as a basic structure, having an acrylamide-substituted cycloalkenyl group at position 4, and further having a limited cyclic substituent at position 5, exhibits a selective inhibiting activity on JAK3. Moreover, the inventors have found that the compound of the present invention exhibits an excellent activity for suppressing the growth of human PBMC, and have also found that the present compound is useful as a pharmaceutical agent for treating various diseases involving JAK3, in particular, autoimmune disease. In addition, the inventors have confirmed that the compound of the present invention has an excellent oral absorbability and is useful as an oral pharmaceutical product. Furthermore, the present inventors have found that the compound of the present invention exhibits an activity of inhibiting IL-2-induced IFN-γ production in vivo, thereby completing the present invention.

The present invention provides the following [1] to [19].
[1] A compound represented by the following formula (I), or a salt thereof:

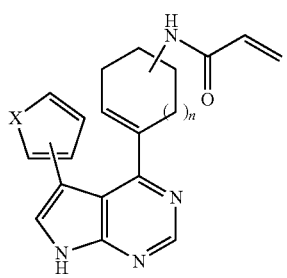
(I)

wherein X represents —CH═CH—, —NH—, a sulfur atom or an oxygen atom; and n represents an integer of 0 to 2.

[2] The compound according to [1] above, or a salt thereof, wherein X is —CH═CH—, a sulfur atom or an oxygen atom, and n is 0 or 1.

[3] The compound according to [1] or [2] above, or a salt thereof, wherein, in the formula (I), the below structure

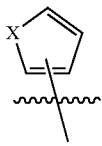

is any one of the following structures:

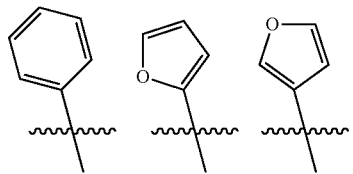

and in the formula (I), the below structure

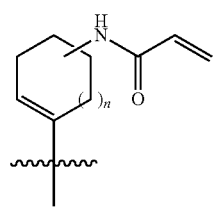

is any one of the following structures:

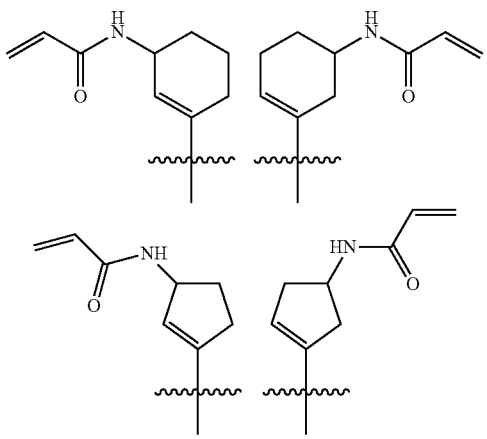

[4] The compound according to any one of [1] to [3] above, or a salt thereof, wherein the compound is N-(3-(5-(furan-2-yl)-7H-pyrrolo[2,3-d]pyrimidin-4-yl)cyclohex-3-en-1-yl)acrylamide or (S)—N-(3-(5-(furan-2-yl)-7H-pyrrolo[2,3-d]pyrimidin-4-yl)cyclohex-3-en-1-yl)acrylamide.

[5] A JAK3 inhibitor comprising, as an active ingredient, the compound according to any one of [1] to [4] or a salt thereof.

[6] A pharmaceutical composition comprising the compound according to any one of [1] to [4] or a salt thereof.

[7] The pharmaceutical composition according to [6], wherein the pharmaceutical composition is a pharmaceutical composition for treating a disease involving JAK3.

[8] An agent for treating rheumatoid arthritis or multiple sclerosis, comprising, as an active ingredient, the compound according to any one of [1] to [4] or a salt thereof.

[9] Use of the compound according to any one of [1] to [4] above or a salt thereof for the production of a JAK3 inhibitor.

[10] Use of the compound according to any one of [1] to [4] above or a salt thereof for the production of a pharmaceutical composition.

[11] The use according to [10] above, wherein the pharmaceutical composition is a pharmaceutical composition for treating diseases involving JAK3.

[12] Use of the compound according to any one of [1] to [4] above or a salt thereof for the production of a therapeutic agent for rheumatoid arthritis or multiple sclerosis.

[13] The compound according to any one of [1] to [4] above or a salt thereof for use in inhibiting JAK3.

[14] The compound according to any one of [1] to [4] above or a salt thereof for use as a pharmaceutical agent.

[15] The compound according to [14] above or a salt thereof, wherein the pharmaceutical agent is a pharmaceutical agent for treating diseases involving JAK3.

[16] The compound according to any one of [1] to [4] above or a salt thereof for use in treating rheumatoid arthritis or multiple sclerosis.

[17] A method for inhibiting JAK3, which comprises administering an effective amount of the compound according to any one of [1] to [4] above or a salt thereof to a subject in need thereof.

[18] A method for treating diseases involving JAK3, which comprises administering an effective amount of the compound according to any one of [1] to [4] above or a salt thereof to a subject in need thereof.

[19] A method for treating rheumatoid arthritis or multiple sclerosis, which comprises administering an effective amount of the compound according to any one of [1] to [4] above or a salt thereof to a subject in need thereof.

Effects of the Invention

According to the present invention, a novel pyrrolo[2,3-d]pyrimidine derivative useful as a selective JAK3 inhibitor, which is represented by the above formula (I), or a salt thereof, is provided.

It has been revealed that the compound of the present invention or a salt thereof exhibits an excellent selective JAK3-inhibiting activity and suppresses the growth of human PBMC based on JAK3 signals. Moreover, the compound of the present invention has an excellent oral absorbability, and it is useful as a pharmaceutical agent, in particular, for oral administration. Accordingly, the compound of the present invention or a salt thereof can treat diseases involving JAK3, such as autoimmune disease, without having serious side effects caused by JAK1 and JAK2 (e.g., lipid increase, anemia, neutropenia, immunosuppression, etc.).

BRIEF DESCRIPTION OF DRAWINGS

FIG. 1 shows IFN-γ production-suppressing effects obtained when Compound 7 and the compound of Comparative Example 12 have been orally administered to mice.

FIG. 2 shows clinical symptom scores obtained when Compound 7, Tofacitinib and Prednisolone have been orally administered to rheumatoid arthritis model mice.

DETAILED DESCRIPTION OF THE INVENTION

The compound of the present invention represented by the above formula (I) is a compound, which comprises pyrrolo[2,3-d]pyrimidine as a basic structure, has a cycloalkenyl group at position 4, and further has a cyclic substituent at position 5, and it is a novel compound, which is not described in any one of the aforementioned prior art documents.

In the present description, the "$C_1$-$C_6$ alkyl group" is a linear or branched saturated hydrocarbon group comprising 1 to 6 carbon atoms, and specific examples of the $C_1$-$C_5$ alkyl group include a methyl group, an ethyl group, an n-propyl group, an isopropyl group, an n-butyl group, an isobutyl group, a sec-butyl group, a tert-butyl group, an n-pentyl group, and an n-hexyl group.

In the compound represented by the formula (I) of the present invention, X represents —CH=CH—, —NH—, a sulfur atom or an oxygen atom. X is preferably —CH=CH—, a sulfur atom or an oxygen atom, more preferably —CH=CH— or an oxygen atom, and particularly preferably an oxygen atom.

In the compound represented by the formula (I) of the present invention, n represents an integer of 0 to 2. n is preferably 0 or 1, and particularly preferably 1.

In the compound represented by the formula (I) of the present invention, specific structures of the below structure

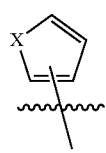

are preferably the following (1) to (5):

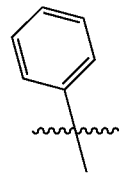 (1)

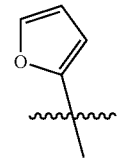 (2)

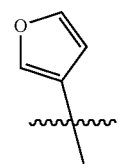 (3)

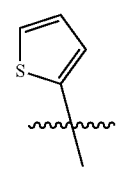 (4)

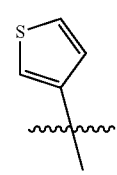 (5)

Among the above (1) to (5), (1), (2) and (3) are more preferable, and (2) is particularly preferable.

In the compound represented by the formula (I) of the present invention, specific structures of the below cycloalkenyl portion

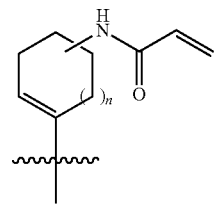

are preferably the following (1) to (10):

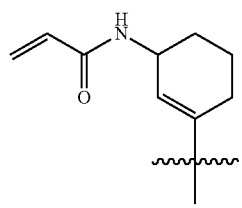 (1)

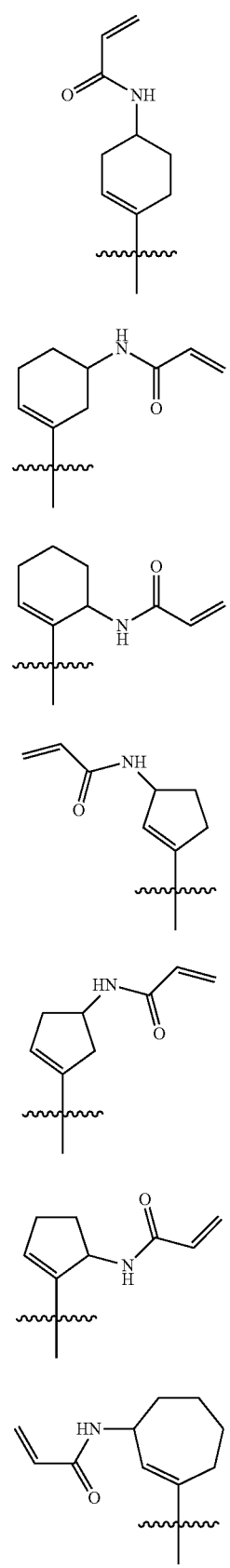

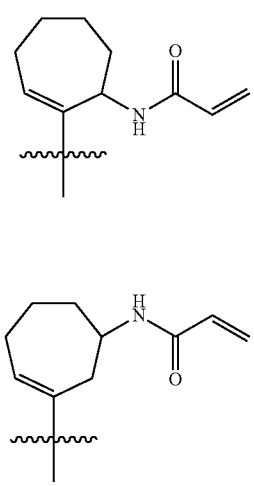

Among the above (1) to (10), (1), (3), (5), (6) and (10) are more preferable, (1), (3), (5) and (6) are even more preferable, (1) and (3) are further preferable, and (3) is particularly preferable.

In the compound represented by the formula (I) of the present invention, a preferred compound is a compound wherein, in the formula (I), X is —CH=CH—, a sulfur atom or an oxygen atom, and n is 0 or 1.

In the compound represented by the formula (I) of the present invention, a more preferred compound is a compound wherein, in the formula (I), the below structure

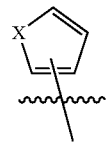

is any one of the following structures:

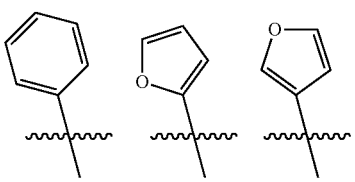

and, in the formula (I), the below structure

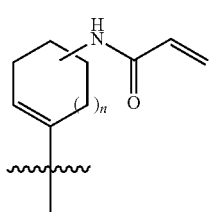

is any one of the following structures:

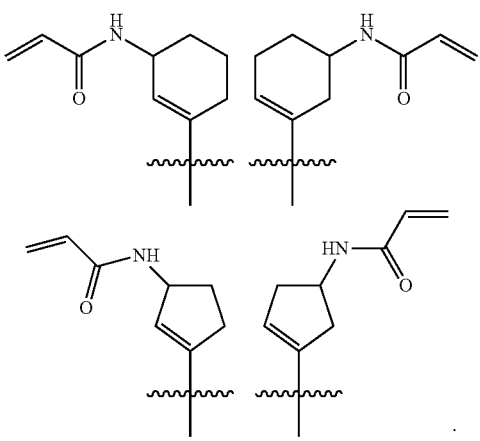

In the compound represented by the formula (I) of the present invention, a further preferred compound is a compound wherein, in the formula (I), X is an oxygen atom and n is 1.

In the compound represented by the formula (I) of the present invention, a particularly preferred compound is a compound wherein, in the formula (I), the below structure

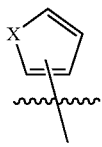

is the following structure:

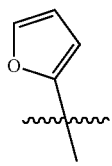

and, in the formula (I), the below structure

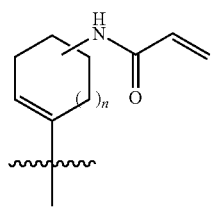

is the following structure:

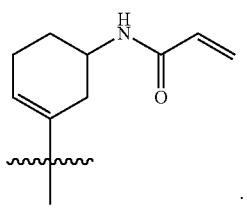 [SMILES: *C1=CCCC(NC(=O)C=C)C1]

Specific examples of the preferred compound of the present invention include the following compounds:

(1) N-(3-(5-phenyl-7H-pyrrolo[2,3-d]pyrimidin-4-yl)cyclohex-3-en-1-yl)acrylamide (Compound 1)

(2) N-(3-(5-(thiophen-2-yl)-7H-pyrrolo[2,3-d]pyrimidin-4-yl)cyclohex-3-en-1-yl)acrylamide (Compound 2)

(3) N-(3-(5-(thiophen-3-yl)-7H-pyrrolo[2,3-d]pyrimidin-4-yl)cyclohex-3-en-1-yl)acrylamide (Compound 3)

(4) N-(3-(5-(furan-3-yl)-7H-pyrrolo[2,3-d]pyrimidin-4-yl)cyclohex-3-en-1-yl)acrylamide (Compound 4)

(5) N-(3-(5-(furan-2-yl)-7H-pyrrolo[2,3-d]pyrimidin-4-yl)cyclohex-3-en-1-yl)acrylamide (Compound 5)

(6) (R)—N-(3-(5-(furan-2-yl)-7H-pyrrolo[2,3-d]pyrimidin-4-yl)cyclohex-3-en-1-yl)acrylamide (Compound 6)

(7) (S)—N-(3-(5-(furan-2-yl)-7H-pyrrolo[2,3-d]pyrimidin-4-yl)cyclohex-3-en-1-yl)acrylamide (Compound 7)

(8) N-(3-(5-(furan-2-yl)-7H-pyrrolo[2,3-d]pyridin-4-yl)cyclopent-3-en-1-yl)acrylamide (Compound 8)

(9) N-(3-(5-phenyl-7H-pyrrole[2,3-d]pyrimidin-4-yl)cyclopent-3-en-1-yl)acrylamide (Compound 9)

(10) N-(3-(5-phenyl-7H-pyrrolo[2,3-d]pyridin-4-yl)cyclopent-2-en-1-yl)acrylamide (Compound 10)

(11) N-(3-(5-phenyl-7H-pyrrolo[2,3-d]pyrimidin-4-yl)cyclohept-3-en-1-yl)acrylamide (Compound 11)

(12) N-(3-(5-phenyl-7H-pyrrolo[2,3-d]pyrimidin-4-yl)cyclohex-2-en-1-yl)acrylamide (Compound 12)

(13) N-(3-(5-(thiophen-2-yl)-7H-pyrrolo[2,3-d]pyridin-4-yl)cyclohex-2-en-1-yl)acrylamide (Compound 13)

(14) N-(3-(5-(thiophen-3-yl)-7H-pyrrolo[2,3-d]pyridin-4-yl)cyclohex-2-en-1-yl)acrylamide (Compound 14)

(15) N-(3-(5-(furan-2-yl)-7H-pyrrolo[2,3-d]pyridin-4-yl)cyclohex-2-en-1-yl)acrylamide (Compound 15) and

(16) N-(3-(5-(furan-3-yl)-7H-pyrrolo[2,3-d]pyridin-4-yl)cyclohex-2-en-1-yl)acrylamide (Compound 16).

Among others, Compounds 2, 5, 7, 8, 9, 13 and 14 are preferable, Compounds 5 and 7 are more preferable, and Compound 7 is particularly preferable.

Next, a method for producing the compound according to the present invention will be described.

The compound represented by the formula (I) of the present invention can be produced, for example, by the following production method.

<Production Method>

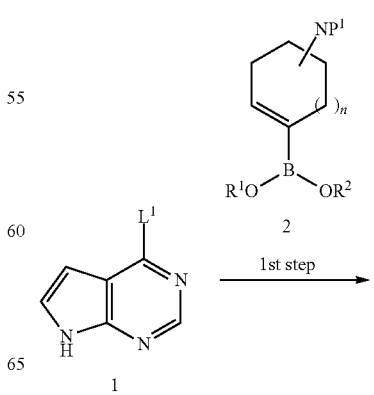

-continued

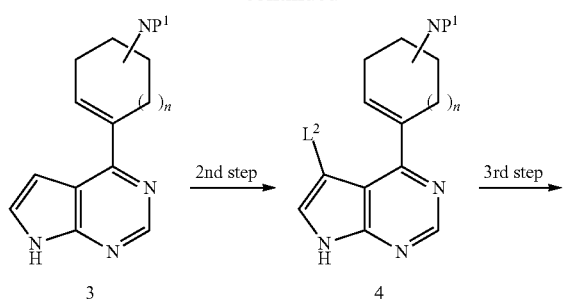

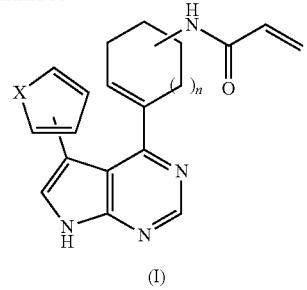

wherein $L_1$ and $L_2$, which are the same or different, each represent a leaving group; $P_1$ and $P_2$ each represent a protective group; $R^1$, $R^2$, $R^3$, $R^4$ and $R^5$, which are the same or different, each represent a hydrogen atom or a $C_1$-$C_6$ alkyl group, wherein $R^1$ and $R^2$, and $R^3$ and $R^4$ may form a ring, together with oxygen and boron atoms adjacent thereto; and other symbols have the same meanings as described above.

$NP^1$ shown in the formula 2, formula 3 to formula 5, formula 8, and formula 9 indicates a state in which a nitrogen atom is protected by the protective group $P^1$. For example, when a tert-butyloxycarbonyl group (Boc group used as a protective group, it means that the nitrogen atom is protected by one or two Boc groups, or it means that an imide such as phthalic imide is formed and the nitrogen is protected thereby.

(Step 1)

The present step is a method of subjecting the compound represented by the formula 1, and the compound represented by the formula 2, which is a commercially available product or can be produced according to a known method, to a coupling reaction to obtain the compound represented by the formula 3.

The present step can be generally carried out according to a known method (for example, Chemical Reviews, Vol. 95, p. 2457, 1995), and it can be carried out, for example, in the presence of a transition metal catalyst and a base, in a solvent which does not adversely affect the reaction.

The boronic acid or boronic acid ester represented by the formula 2 can be used in an amount of 1 to 10 equivalents, and preferably 1 to 3 equivalents, based on the amount of the compound represented by the formula 1 (1 mole).

Examples of the transition metal catalyst used herein include palladium catalysts (e.g., palladium acetate, palladium chloride, and tetrakis(triphenylphosphine)palladium) and nickel catalysts (e.g., nickel chloride). As necessary, a ligand (e.g., triphenylphosphine and tri-tert-butylphosphine) is added to the catalyst, and a metal oxide (e.g., copper oxide and silver oxide) and the like may be used as a co-catalyst.

The amount of the transition metal catalyst used is different depending on the type of the catalyst, and the transition metal catalyst is used in an amount of generally about 0.0001 to 1 mole, and preferably about 0.01 to 0.5 moles, based on the amount of the compound represented by the formula 1 (1 mole). The ligand is used in an amount of generally about 0.0001 to 4 moles, and preferably about 0.01 to 2 moles, based on the amount of the compound represented by the formula 1 (1 mole), and the co-catalyst is used in an amount of generally about 0.0001 to 4 moles, and preferably about 0.01 to 2 moles, based on the amount of the compound represented by the formula 1 (1 mole).

Examples of the base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkaline metal alkoxides (e.g., sodium methoxide, sodium ethoxide, sodium tert-butoxide, and potassium tert-butoxide), and alkaline metal disilazides (e.g., lithium disilazide, sodium disilazide, and potassium disilazide).

The base is used in an amount of generally 0.1 to 10 moles, and preferably about 1 to 5 moles, based on the amount of the compound represented by the formula 1 (1 mole).

The solvent is not particularly limited, as long as it does not adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., 1,4-dioxane, dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is 0.1 to 100 hours, and preferably 0.5 to 24 hours. The reaction temperature is 0° C. to the boiling point of the solvent, and preferably 0° C. to 150° C.

The thus obtained compound represented by the formula 3 can be subjected to the subsequent step, after being isolated and purified according to known separation and purification means, as described later, or without such isolation and purification.

(Step 2)

The present step is a method of halogenating the compound represented by the formula 3 to obtain the compound represented by the formula 4. The halogenation can be carried out, for example, by a method of using fluorine, chlorine, bromine, iodine, etc., or a method of using N-chlorosuccinimide, N-bromosuccinimide or N-iodosuccinimide. In the present reaction, a method of using N-chlorosuccinimide, N-bromosuccinimide, N-iodosuccinimide, etc. is preferable.

Such N-chlorosuccinimide, N-bromosuccinimide, N-iodosuccinimide, etc. can be used in an amount of 1 to 10 equivalents, and preferably 1 to 3 equivalents, based on the amount of the compound represented by the formula 3 (1 mole).

The solvent is not particularly limited, as long as it does not affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is 0.1 to 100 hours, and preferably 0.5 to 24 hours. The reaction temperature is 0° C. to the boiling point of the solvent, and preferably 0° C. to 100° C.

The thus obtained compound represented by the formula 4 can be isolated and purified by a known separation purification means, as described later, or it can be subjected to the subsequent step without such isolation and purification.

(Step 3)

The present step is a method of introducing a protective group $P^2$ into the compound represented by the formula 4 to obtain the compound represented by the formula 5.

The protection can be carried out by a generally known method, for example, the method described in Protective Groups in Organic Synthesis, T. W. Greene, John Wiley & Sons (1981), or a method equivalent thereto. In the present reaction, a protective group $P^2$ is preferably a toluenesulfonate group, a benzenesulfonate group, a methanesulfonate group, a methoxymethyl group, a trityl group, and the like.

Examples of the protective group agent used in the present reaction include toluenesulfonyl chloride, benzenesulfonyl chloride, methanesulfonyl chloride, chloro(methoxy)methane, and trityl chloride. Such a protective group agent is used in an amount of generally about 1 to 100 moles, and preferably about 1 to 10 moles, based on the amount of the compound represented by the formula 4 (1 mole).

Examples of the base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkaline metal alkoxides (e.g., sodium methoxide, sodium ethoxide, sodium tert-butoxide, and potassium tert-butoxide), and alkaline metal disilazides (e.g., lithium disilazide, sodium disilazide, and potassium disilazide).

The base is used in an amount of generally 0.1 to 100 moles, and preferably about 1 to 10 moles, based on the amount of the compound represented by the formula 4 (1 mole).

The solvent is not particularly limited, as long as it does not affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., dimethoxyethane and tetrahydrofuran), alcohols (e.g., methanol and ethanol), aprotic polar solvents (e.g., dimethylformamide, dimethyl sulfoxide, and hexamethylphosphoramide), water, and the mixtures thereof.

The reaction time is 0.1 to 100 hours, and preferably 0.5 to 24 hours. The reaction temperature is 0° C. to the boiling point of the solvent, and preferably 0° C. to 100° C.

The thus obtained compound represented by the formula 5 can be isolated and purified by a known separation purification means, as described later, or it can be subjected to the subsequent step without such isolation and purification.

(Step 4)

The present step is a method of subjecting the compound represented by the formula 5 and the boronic acid or boronic acid ester represented by the formula 6, which is a commercially available product or can be produced by a known method, to a coupling reaction, or subjecting the compound represented by the formula 5 and the organic tin compound represented by the formula 7, which is a commercially available product or can be produced by a known method, to a coupling reaction, so as to obtain the compound represented by the formula 8.

The present step can be carried out by the same method as that in Step 1.

(Step 5)

The present step is a method of deprotecting the protective group $P^2$ of the compound represented by the formula 8 to obtain the compound represented by the formula 9. The deprotection can be carried out by a generally known method, for example, the method described in Protective Groups in Organic Synthesis, T. W. Greene, John Wiley & Sons (1981), or a method equivalent thereto.

For example, when a p-toluenesulfonic acid group is used as a protective group $P^2$, it is preferable to use a deprotecting agent such as lithium hydroxide, sodium hydroxide, potassium hydroxide or tetrabutylammonium fluoride. Such a deprotecting agent is used in an amount of generally 0.5 to 100 moles, and preferably approximately 1 to 10 moles, based on the amount of the compound represented by the formula 8 (1 mole).

Moreover, when a trityl group is used as a protective group $P^2$, it is preferable to use a deprotecting agent such as lithium hydroxide, sodium hydroxide, potassium hydroxide, tetrabutylammonium fluoride, acid (e.g., hydrochloric acid, trifluoroacetic acid, acetic acid, and sulfuric acid). Such a deprotecting agent is used in an amount of generally 0.5 to 100 moles, and preferably about 1 to 10 moles, based on the amount of the compound represented by the formula 8 (1 mole).

The solvent used in the reaction is not particularly limited, as long as it does not adversely affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is 0.1 to 100 hours, and preferably 0.5 to 24 hours. The reaction temperature is 0° C. to the boiling point of the solvent, and preferably 0° C. to 100° C.

The thus obtained compound of the formula 9 can be isolated and purified by a known separation purification means, as described later, or it can be subjected to the subsequent step without such isolation and purification.
(Step 6)

The present step is a method of deprotecting the protective group $P^1$ for the amino group of the compound represented by the formula 9 to obtain the compound represented by the formula 10. The deprotection can be carried out by a generally known method, for example, the method described in Protective Groups in Organic Synthesis, T. W. Greene, John Wiley & Sons (1981), or a method equivalent thereto.

When a tert-butyloxycarbonyl group is used as a protective group $P^1$, the deprotection is preferably carried out under acidic conditions. Examples of the acid include hydrochloric acid, acetic acid, trifluoroacetic acid, sulfuric acid, and tosic acid. The acid is used in an amount of preferably about 1 to 100 equivalents based on the amount of the compound represented by the formula 9 (1 mole).

The solvent used in the reaction is not particularly limited, as long as it does not affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is 0.1 to 100 hours, and preferably 0.5 to 24 hours. The reaction temperature is 0° C. to 100° C., and preferably 0° C. to 50° C.

The thus obtained compound represented by the formula 10 can be isolated and purified by a known separation purification means, as described later, or it can be subjected to the subsequent step without such isolation and purification.
(Step 7)

The present step is a method of subjecting the amino group of the compound represented by the formula 10 to an amidation reaction with acrylic acid or an acrylic acid halide, so as to obtain the compound represented by the formula (I) of the present invention.

When acrylic acid is used, the acrylic acid is used in an amount of generally 0.5 to 10 moles, and preferably approximately 1 to 5 moles, based on the amount of the compound represented by the formula 10 (1 mole), in the presence of a condenser.

Example of the condenser include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), benzotriazol-1-yl-oxytrisdimethylaminophosphonium hexafluorophosphate (BOP), benzotriazol-1-yl-oxytrispyrrolidinophosphonium hexafluorophosphate (PyBOP), 7-azabenzotriazol-1-yloxytrispyrrolidinophosphonium phosphate (PyAOP), bromotrispyrrolidinophosphbnium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), 0-(7-azabenzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). Examples of the additive used herein include 1-hydroxybenzotriazole (HOBt), 1-hydroxy-7-azabenzotriazole (HOAt), and N-hydroxysuccinimide (HOSu).

Such a substance is used in an amount of generally 1 to 100 moles, and preferably about 1 to 10 moles, based on the amount of the compound represented by the formula 10 (1 mole).

In addition, a base can be added, as necessary.

Examples of such a base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide).

The base is used in an amount of generally 1 to 100 moles, and preferably about 1 to 10 moles, based on the amount of the compound represented by the formula 10 (1 mole).

The solvent used in the reaction is not particularly limited, as long as it does not affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is 0.1 to 100 hours, and preferably 0.5 to 24 hours. The reaction temperature is 0° C. to the boiling point of the solvent, and preferably 0° C. to 100° C.

When an acrylic acid halide is used, the acid halide is used in an amount of generally 0.5 to 10 moles, and preferably approximately 1 to 5 moles, based on the amount of the compound represented by the formula 10 (1 mole). It is to be noted that the acid halide is a commercially available product or can be produced according to a known method.

In addition, a base can be added, as necessary. Examples of such a base include organic amines (e.g., trimethylamine, triethylamine, diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide).

and purification means include concentration, vacuum concentration, solvent extraction, recrystallization, reprecipitation, preparatory reverse-phase high-performance liquid chromatography, column chromatography, and preparatory thin-layer chromatography.

When the compound of the present invention has an optical isomer, a stereoisomer, a tautomer or a rotational isomer, all of these isomers and the mixtures thereof are included in the compound of the present invention. Moreover, the compound of the present invention also includes a racemate, or an optically active substance resolved from the racemate.

Moreover, the compound of the present invention also includes the following tautomers.

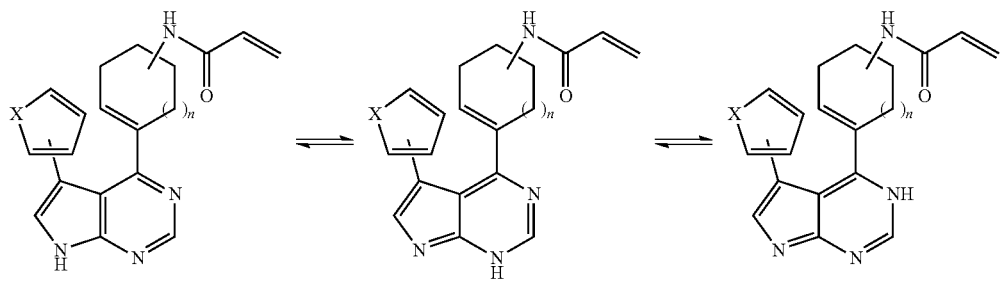

The base is used in an amount of generally 1 to 100 moles, and preferably about 1 to 10 moles, based on the amount of the compound represented by the formula 10 (1 mole).

The solvent used in the reaction is not particularly limited, as long as it does not affect the reaction. Examples of the solvent used herein include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), and the mixtures thereof.

The reaction time is 0.1 to 100 hours, and preferably 0.5 to 24 hours. The reaction temperature is 0° C. to the boiling point of the solvent, and preferably 0° C. to 100° C.

In the above described production method, "connection of a pyrrolopyrimidine skeleton with the compound represented by the formula 2" (Step 1) and "introduction of the compound represented by the formula 6 or the formula 7 into the pyrrolopyrimidine skeleton" (Step 4) are carried out, successively. However, this order can be changed.

That is to say, the compound can also be synthesized in the order of "introduction of the compound represented by the formula 6 or the formula 7 into a pyrrolopyrimidine skeleton" (Step 4) and then, "connection of the pyrrolopyrimidine skeleton with the compound represented by the formula 2" (Step 1).

Specifically, the compound represented by the formula 1 is subjected to individual steps in the order of Step 2, Step 3, Step 4 and Step 1, so that the compound can be induced to the compound represented by the formula 8. Conditions applied in each step are the same as those described above.

The thus obtained compound represented by the formula (I) of the present invention and an intermediate thereof can be easily isolated and purified according to known separation and purification means. Examples of such separation The compound of the present invention or a salt thereof may be a crystal. Even if the crystal form is a single form or a polymorphic mixture, the crystal is included in the compound of the present invention or a salt thereof. Such a crystal can be produced by crystallizing the present compound according to a known crystallization method. The compound of the present invention or a salt thereof may be either a solvate (for example, a hydrate), or a non-solvate, and both of them are included in the compound of the present invention or a salt thereof. Compounds labeled with isotopes (for example, deuterium, $^3$H, $^{13}$C, $^{14}$C, $^{35}$S, and $^{125}$I) or the like are also included in the compound of the present invention or a salt thereof.

A prodrug of the compound of the present invention or a salt thereof is also included in the present invention. The prodrug means a compound, which is converted to the compound of the present invention or a salt thereof as a result of a reaction with enzyme, gastric acid or the like under in vivo physiological conditions; namely, a compound, which causes enzymatic oxidation, reduction, hydrolysis or the like, so that it is changed to the compound of the present invention or a salt thereof, or a compound, which undergoes hydrolysis or the like by the action of gastric acid or the like, so that it is changed to the compound of the present invention or a salt thereof. Moreover, such a prodrug of the compound of the present invention or a salt thereof may also be a compound, which changes to the compound of the present invention or a salt thereof under physiological conditions as described in "Iyakuhin no Kaihatsu (Development of Pharmaceutical Products)," Vol. 7, Bunshi Sekkei (Molecular Designing), pp. 163-198, published by Hirokawa Shoten, 1990.

A salt of the compound of the present invention is not particularly limited, as long as it is a pharmaceutically acceptable salt, and it means a salt commonly used in the field of organic chemistry. Examples of such a salt include salts, such as a base-added salt in a carboxy group when the present compound has the carboxy group, or an acid-added salt in an amino group or a basic heterocyclic group when the present compound has the amino group or the basic heterocyclic group.

Examples of the base-added salt include: alkaline metal salts such as a sodium salt or a potassium salt; alkaline-earth metal salts such as a calcium salt or a magnesium salt; ammonium salts; and organic amine salts such as a trimethylamine salt, a triethylamine salt, a dicyclohexylamine salt, an ethanolamine salt, a diethanolamine salt, a triethanolamine salt, a procaine salt, and an N,N'-dibenzylethylenediamine salt.

Examples of the acid-added salt include: inorganic acid salts such as a hydrochloride, a sulfate, a nitrate, a phosphate, or a perchlorate; organic acid salts such as an acetate, a formate, maleate, a fumarate, a tartrate, a citrate, an ascorbate, or a trifluoroacetate; and sulfonates such as a methanesulfonate, an isethionate, a benzenesulfonate, or a p-toluenesulfonate.

The compound of the present invention or a salt thereof exhibits a higher selective inhibiting activity on JAK3, than on JAK1 and JAK2. In addition, the compound of the present invention or a salt thereof has an excellent action to suppress the growth of human PBMC. Furthermore, the compound of the present invention or a salt thereof exhibits an inhibitory activity on IL-2-induced IFN-γ production in vivo.

Since the compound of the present invention or a salt thereof exhibits an excellent JAK3-inhibiting activity, it is useful as a pharmaceutical agent for treating a disease involving JAK3. Moreover, since the compound of the present invention or a salt thereof has excellent selectivity to JAK3, it is useful as a pharmaceutical agent with reduced side effects, which are caused by JAK1 and JAK2 (i.e., lipid rise, anemia, neutropenia, immunosuppression, etc.).

The "a disease involving JAK3" is a disease, the incidence of which is decreased and the symptoms of which achieve an alleviation and a remission, are alleviated, and/or are completely recovered by deleting, suppressing and/or inhibiting the function of JAK3. Examples of such a disease involving JAK3 include autoimmune disease (rheumatoid arthritis, multiple sclerosis, systemic lupus erythematosus, scleroderma, polymyositis/dermatomyositis, Sjogren's syndrome, Behcet's disease, etc.), allergic disease (bronchial asthma, allergic rhinitis/hay fever, atopic dermatitis, food allergy, anaphylaxis, drug allergy, hives, conjunctivitis, etc.), nervous system disease (multiple sclerosis, Alzheimer's disease, etc.), inflammatory bowel disease (ulcerative colitis, Crohn's disease), psoriasis, contact dermatitis, diabetes, celiac disease, viral infectious disease, acute respiratory distress syndrome (ARDS), graft-versus-host disease (GVHD), transplant rejection, hematologic malignancy (lymphoma, leukemia), and other malignant tumors. Among these diseases, psoriasis, graft-versus-host disease, multiple sclerosis, inflammatory bowel disease, systemic lupus erythematosus and rheumatoid arthritis are preferable, and rheumatoid arthritis or multiple sclerosis is more preferable.

In the present description, the "treatment" includes prevention and/or treatment of the above described diseases involving JAK3, and also, alleviation of symptoms and/or maintenance for prevention of recurrence.

When the compound of the present invention or a salt thereof is used as a pharmaceutical agent, a pharmaceutical carrier can be mixed into the present compound, as necessary, and various dosage forms can be adopted depending treatment purpose. As such a dosage form, any one of an oral agent, an injection, a suppository, an ointment, an inhalant, a patch and the like may be adopted. Since the compound of the present invention or a salt thereof has excellent oral absorbability, an oral agent is preferably adopted. These dosage forms can be produced by commonly used formulation methods, which are known to a person skilled in the art.

As such pharmaceutical carriers, various types of organic or inorganic carrier substances, which are commonly used as preparation materials, are used. Such a carrier is mixed as an excipient, a binder, a disintegrator or a lubricant into a solid preparation, and is also mixed as a solvent, a solubilizer, a suspending agent, a tonicity agent, a buffer, a soothing agent and the like into a liquid preparation. In addition, preparation additives such as an antiseptic, an antioxidant, a coloring agent, a sweetener or a stabilizer can also be used, as necessary.

In the case of preparing a solid preparation for oral use, an excipient, and as necessary, an excipient, a binder, a disintegrator, a lubricant, a coloring agent, a flavoring agent and the like are added to the compound of the present invention, and thereafter, a tablet, a coated tablet, a granule, a powder agent, a capsule, and the like can be produced by an ordinary method.

In the case of preparing an injection, a pH adjuster, a buffer, a stabilizer, a tonicity agent, a local anesthetic and the like are added to the compound of the present invention, and thereafter, subcutaneous, intramuscular, and intravenous injections can be produced by an ordinary method.

The amount of the compound of the present invention to be mixed into each of the aforementioned dosage unit forms is not constant, and it depends on the symptoms of a patient to whom the present compound is to be applied, or the dosage form or the like. In general; the compound of the present invention is desirably used at a dose of approximately 0.05 to 1,000 mg per dosage unit form in the case of an oral agent, and at a dose of approximately 0.01 to 500 mg in the case of injection, and at a dose of approximately 1 to 1,000 mg in the case of a suppository.

The applied dose of a drug having the aforementioned dosage form is different depending on the symptoms, body weight, age, sex and the like of a patient, and it cannot be unconditionally determined. The compound of the present invention may be generally applied at a dose of approximately 0.05 to 5,000 mg, and preferably 0.1 to 1,000 mg, per adult (body weight: 50 kg) per day. This dose is preferably administered to a patient once a day, or divided over 2 or 3 administrations.

EXAMPLES

Hereinafter, the present invention will be described in detail in the following examples. However, these examples are not intended to limit the scope of the present invention. Various types of reagents used in the examples are commercially available products, unless otherwise specified. For silica gel chromatography, Biotage SNAP Cartridge Ultra manufactured by Biotage was used, and for basic silica gel chromatography, Biotage SNAP Cartridge KP-NH manufactured by Biotage was used.

For preparatory thin-layer chromatography, Kieselgel TM60F254, Art. 5744 manufactured by Merck, or NH2 Silica Gel 60F254 Plate Wako manufactured by Wako Pure Chemical Industries, Ltd. was used.

For $^1H$-NMR, AL400 (400 MHz) manufactured by JEOL, Mercury (400 MHz) manufactured by Varian, or Inova (400 MHz) manufactured by Varian was used, and the measurement was carried out using tetramethylsilane as a standard substance. In addition, for mass spectrum, Micromass ZQ or SQD manufactured by Waters was used, and the measurement was carried out according to an electrospray ionization method (ESI) or an atmospheric pressure chemical ionization method (APCI). A microwave reaction was carried out using Initiator manufactured by Biotage.

Individual abbreviations have the following meanings.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
Boc: tert-butoxycarbonyl
DMSO-$d_6$: deuterated dimethyl sulfoxide
CDCl$_3$: deuterated chloroform
CD$_3$OD: deuterated methanol
THF: tetrahydrofuran
DMF: N,N-dimethylformamide
DMSO: dimethyl sulfoxide
Pd(PPh$_3$)$_4$: tetrakis(triphenylphosphine)palladium
PdCl$_2$(dppf)CH$_2$Cl$_2$: [1,1'-bis(diphenylphosphino)ferrocene]dichloropalladium(II) dichloromethane complex
PdCl$_2$(PPh$_3$)$_2$: dichlorobis(triphenylphosphine)palladium (II)

Reference Example 1

Reference Example 1(1a) 5-((tert-Butoxycarbonyl) amino)cyclohex-1-en-1-yl trifluoromethanesulfonate Reference Example 1(1b) 3-((tert-Butoxycarbonyl) amino)cyclohex-1-en-1-yl trifluoromethanesulfonate tert-Butyl (3-oxocyclohexyl)carbamate (5.0 g) and N-phenyl-bis(trifluoromethanesulfonimide) (11.0 g) were dissolved in THF (100 mL), and the obtained solution was then cooled to −78° C. Thereafter, a THF solution (26.0 mL) of 2.0 M lithium diisopropylamide was added to the reaction solution, the temperature of the mixed solution was increased to 0° C., and the mixed solution was then stirred for 30 minutes. Thereafter, a 0.5 M potassium hydrogen sulfate aqueous solution was added to the reaction mixture for dilution, and the obtained solution was then extracted with ethyl acetate. The gathered organic layer was washed with a saturated saline, was then dried over anhydrous sodium sulfate, and was then concentrated under a reduced pressure. The obtained residue was purified by silica gel chromatography (hexane:ethyl acetate) to obtain each of the compound (4.39 g, yield: 54%) of Reference Example 1(1a), and the compound (2.00 g, yield: 25%) of Reference Example 1(1b).

Reference Example 1(1a): $^1$H NMR (CDCl$_3$) δ: 5.84-5.74 (m, 1H), 4.74-4.46 (m, 1H), 4.06-3.85 (m, 1H), 2.77-2.63 (m, 1H), 2.38-2.18 (m, 3H), 1.90-1.80 (m, 1H), 1.66-1.53 (m, 1H), 1.45 (s, 9H)
ESI-MS m/z 346 (MH$^+$)

Reference Example 1(1b): $^1$H NMR (CDCl$_3$) δ: 5.79-5.72 (m, 1H), 4.70-4.50 (m, 1H), 4.47-4.33 (m, 1H), 2.40-2.25 (m, 2H), 1.94-1.67 (m, 3H), 1.56-1.49 (m, 1H), 1.45 (s, 9H)
ESI-MS m/z 346(MH$^+$)

Reference Example 1(2a) tert-Butyl (3-(4,4,5,5-tetramethyl-1,3,2-dioxaborolan-2-yl)cyclohex-3-en-1-yl)carbamate DMF (90 mL) was added to the compound (9.25 g) of Reference Example 1(1a), 4,4,4',4',5,5,5',5'-octamethyl-2,2'-bi(1,3,2-dioxaborolane) (10.2 g) and potassium acetate (3.95 g), followed by nitrogen substitution. Thereafter, PdCl$_2$(dppf)CH$_2$Cl$_2$ (980 mg) was added to the resultant, and the obtained mixture was then stirred at 80° C. for 14 hours. Thereafter, the reaction mixture was cooled to a room temperature, and ethyl acetate and water were then added to the mixture. Thereafter, the thus obtained mixture was filtered through Celite. The filtrate was extracted with ethyl acetate, and thereafter, the gathered organic layer was washed with water and then with a saturated saline. The resultant was dried over anhydrous sodium sulfate, and was then concentrated under a reduced pressure. The obtained residue was purified by silica gel chromatography (hexane:ethyl acetate) to obtain a product of interest (6.51 g, yield: 75%).

$^1$H NMR (CDCl$_3$) δ: 6.56-6.51 (m, 1H), 4.58-4.41 (m, 1H), 3.80-3.62 (m, 1H), 2.58-2.41 (m, 1H), 2.31-2.13 (m, 2H), 1.98-1.77 (m, 2H), 1.54-1.47 (m, 1H), 1.44 (s, 9H), 1.25 (s, 12H)
ESI-MS m/z 324 (MH$^+$)

Reference Example 1(2b) tert-Butyl (3-(4,4,5,5-tetramethyl-1,3,2-dioxaborolan-2-yl)cyclohex-2-en-1-yl)carbamate A product of interest was obtained in accordance with Reference Example 1(2a), with the exception that the compound of Reference Example 1(1b) was used instead of the compound of Reference Example 1(1a).

$^1$H NMR (CDCl$_3$) δ: 6.40-6.32 (m, 1H), 4.53 (d, J=7.3 Hz, 1H), 4.27-4.14 (m, 1H), 2.11-2.02 (m, 2H), 1.97-1.83 (m, 1H), 1.68-1.52 (m, 2H), 1.49-1.44 (m, 1H), 1.44 (s, 9H), 1.26 (s, 12H)
ESI-MS m/z 324(MH$^+$)

Reference Example 2

Reference Example 2(1a) 4-((tert-Butoxycarbonyl) amino)cyclopent-1-en-1-yl trifluoromethanesulfonate Reference Example 2(1b) 3-((tert-Butoxycarbonyl) amino)cyclopent-1-en-1-yl trifluoromethanesulfonate Under a nitrogen atmosphere, a THF solution (114 mL) of 1.0 M lithium hexamethyldisilazide was added to THF (100 mL), and the obtained mixture was then cooled to −78° C. A THF (100 mL) solution of tert-butyl (3-oxocyclopentyl) carbamate (9.0 g) was added to the reaction solution over 10 minutes. Thereafter, N-phenyl-bis(trifluoromethanesulfonimide) (19.4 g) was added to the mixture, and the temperature of the obtained mixture was then increased to 0° C., followed by stirring for 10 minutes. Thereafter, water, toluene, and a 5 M sodium hydroxide aqueous solution were added to the reaction mixture, and the obtained mixture was then stirred at a room temperature for 30 minutes. Thereafter, the reaction mixture was extracted with toluene. The gathered organic layer was successively washed with a 0.5 M potassium hydrogen sulfate aqueous solution, a saturated sodium hydrogen carbonate aqueous solution and a saturated saline, and was then dried over anhydrous sodium sulfate, followed by vacuum concentration. The obtained residue was purified by silica gel chromatography (hexane:ethyl acetate) to obtain each of the compound (8.61 g, yield: 58%) of Reference Example 2(1a) and the compound (4.31 g, yield: 29%) of Reference Example 2(1b).

Reference Example 2(1a): $^1$H R(CDCl$_3$) δ: 5.62-5.56 (m, 1H), 4.87-4.67 (m, 1H), 4.49-4.23 (m, 1H), 3.07-2.76 (m, 2H), 2.50-2.40 (m, 1H), 2.32-2.20 (m, 1H), 1.45 (s, 9H)

ESI-MS m/z 332(MH$^+$)

Reference Example 2(1b): $^1$H NMR (CDCl$_3$) δ: 5.68-5.61 (m, 1H), 4.89-4.70 (m, 1H), 4.69-4.48 (m, 1H), 2.75-2.43 (m, 3H), 1.84-1.66 (m, 1H), 1.45 (s, 9H)

ESI-MS m/z 332(MH$^+$)

Reference Example 2(2a) tert-Butyl (3-(4,4,5,5-tetramethyl-1,3,2-dioxaborolan-2-yl)cyclopent-3-en-1-yl)carbamate A product of interest was obtained in accordance with Reference Example 1(2a), with the exception that the compound of Reference Example 2(1a) was used instead of the compound of Reference Example 1(1a).

$^1$H NMR (CDCl$_3$) δ: 6.50-6.45 (m, 1H), 4.76-4.58 (m, 1H), 4.37-4.19 (m, 1H), 2.86-2.70 (m, 2H), 2.37-2.22 (m, 2H), 1.43 (s, 9H), 1.27 (s, 12H)

ESI-MS m/z 310(MH$^+$)

Reference Example 2(2b) tert-Butyl (3-(4,4,5,5-tetramethyl-1,3,2-dioxaborolan-2-yl)cyclopent-2-en-1-yl)carbamate A product of interest was obtained in accordance with Reference Example 1(2a), with the exception that the compound of Reference Example 2(1b) was used instead of the compound of Reference Example 1(1a).

$^1$H NMR (CDCl$_3$) δ: 6.42-6.32 (m, 1H), 4.84-4.69 (m, 1H), 4.58-4.39 (m, 1H), 2.58-2.46 (m, 1H), 2.44-2.25 (m, 2H), 1.55-1.47 (m, 1H), 1.44 (s, 9H), 1.27 (s, 12H)

ESI-MS m/z 310(MH$^+$)

Reference Example 3 (S)-tert-Butyl (3-(4,4,5,5-tetramethyl-1,3,2-dioxaborolan-2-yl)cyclohex-3-en-1-yl)carbamate

Reference Example 3(1) tert-Butyl ((1S,3R)-3-hydroxycyclohexyl)carbamate (1R,3S)-3-Aminocyclohexanol (13.7 g) was dissolved in 2-methyltetrahydrofuran (140 mL), and a saturated sodium hydrogen carbonate aqueous solution (70 mL) was then added to the obtained solution. Thereafter, di-tert-butyl dicarbonate (27.5 g) was added to the reaction mixture at 0° C., and the obtained mixture was then stirred at a room temperature for 16 hours. Thereafter, water was added to the reaction mixture for dilution, and the obtained mixture was then extracted with 2-methyltetrahydrofuran. The gathered organic layer was washed with a saturated ammonium chloride aqueous solution, a saturated sodium hydrogen carbonate aqueous solution and a saturated saline, and was then dried over anhydrous sodium sulfate, followed by vacuum concentration. The obtained solid was washed with heptane to obtain a product of interest (22.7 g, yield: 89%).

$^1$H NMR (CDCl$_3$) δ: 4.82-4.58 (m, 1H), 3.82-3.66 (m, 1H), 3.63-3.40 (m, 1H), 2.25-2.11 (m, 1H), 1.93-1.74 (m, 3H), 1.62-1.55 (m, 1H), 1.44 (s, 9H), 1.39-1.04 (m, 4H)

ESI-MS m/z 216 (MH$^+$)

Reference Example 3(2) (S)-tert-Butyl (3-oxocyclohexyl)carbamate

The compound (21.5 g) of Reference Example 3(1) was dissolved in ethyl acetate (200 mL), and thereafter, 1-methyl-2-azaadamantane N-oxyl (166 mg), a 5 M sodium bromide aqueous solution (6 mL) and a saturated sodium hydrogen carbonate aqueous solution (100 mL) were successively added to the above obtained solution. Thereafter, a 10% sodium hypochlorite aqueous solution (100 mL) was added to the mixed solution at 0° C., and the obtained mixture was then stirred for 1 hour. Thereafter, a 10% sodium hydrogen sulfite aqueous solution was added to the reaction mixture at 0° C., and the obtained mixture was diluted with a 10% potassium carbonate aqueous solution and was then extracted with ethyl acetate. The gathered organic layer was washed with 1 M hydrochloric acid, a saturated sodium hydrogen carbonate aqueous solution, water and a saturated saline, and was then dried over anhydrous sodium sulfate, followed by vacuum concentration. The obtained solid was washed with diisopropyl ether-heptane to obtain a product of interest (19.4 g, yield: 91%).

$^1$H NMR (CDCl$_3$) δ: 4.67-4.35 (m, 1H), 4.05-3.77 (m, 1H), 2.76-2.64 (m, 1H), 2.43-2.19 (m, 3H), 2.14-1.92 (m, 2H), 1.79-1.64 (m, 2H), 1.44 (s, 9H)

ESI-MS m/z 214 (MH$^+$)

Reference Example 3(3) (S)-5-((tert-Butoxycarbonyl)amino)cyclohex-1-en-1-yl trifluoromethanesulfonate A THF (160 mL) solution of the compound (32.3 g) of Reference Example 3(2) was added dropwise to a THF solution (780 mL) of sodium bis(trimethylsilyl)amide (60.5 g), which had been cooled to −78° C., and the reaction mixture was then stirred for 30 minute. N-phenyl-bis(trifluoromethanesulfonimide) (64.3 g) was added to the reaction mixture at −78° C., and the obtained mixture was then stirred for 30 minutes. Thereafter, the temperature of the reaction mixture was increased to 0° C., and the mixture was further stirred for 2 hours. Thereafter, water and a 1 M sodium hydroxide aqueous solution were added to the reaction mixture, the temperature of the obtained mixture was then increased to a room temperature, and the mixture was then extracted with toluene. The gathered organic layer was washed with a 1 M potassium hydrogen sulfate aqueous solution, a saturated sodium hydrogen carbonate aqueous solution, water and a saturated saline, and was then dried over anhydrous sodium sulfate, followed by vacuum concentration. Heptane was added to the obtained residue, and the precipitated solid was collected by filtration and was then washed with heptane to obtain a product of interest (41.6 g, yield: 79%).

$^1$H NMR (CDCl$_3$) δ: 5.84-5.74 (m, 1H), 4.74-4.46 (m, 1H), 4.06-3.85 (m, 1H), 2.77-2.63 (m, 1H), 2.38-2.18 (m, 3H), 1.90-1.80 (m, 1H), 1.66-1.53 (m, 1H), 1.45 (s, 9H)

ESI-MS m/z 346 (MH$^+$)

Reference Example 3(4) (S)-tert-Butyl (3-(4,4,5,5-tetramethyl-1,3,2-dioxaborolan-2-yl)cyclohex-3-en-1-yl)carbamate To a toluene (450 mL) solution of the compound (32.8 g) of Reference Example 3(3), bis(pinacolato)diboron (26.5 g), potassium acetate (28.0 g), triphenylphosphine (2.49 g) and PdCl₂(PPh₃)₂ (3.33 g) were successively added. The temperature of the obtained mixture was increased to 60° C., and the mixture was then stirred under a nitrogen atmosphere for 4 hours. Thereafter, the reaction mixture was cooled to a room temperature, toluene was then added to the mixture, and thereafter the thus obtained mixture was filtered through Celite. The filtrate was washed with a 1 M sodium hydroxide aqueous solution, 1 M hydrochloric acid, a saturated sodium hydrogen carbonate aqueous solution, water and a saturated saline, and was then dried over anhydrous sodium sulfate, followed by vacuum concentration. Ethyl acetate-heptane and activated carbon were added to the obtained residue, and the obtained mixture was left for 1 hour and was then filtered through Celite. The filtrate was concentrated under a reduced pressure, and cyclohexane-heptane was then added to the obtained residue. The precipitated solid was collected by filtration and was then washed with cyclohexane-heptane to obtain a product of interest (21.3 g, yield: 69%).

$^1$H NMR (CDCl₃) δ: 6.56-6.51 (m, 1H), 4.58-4.41 (m, 1H), 3.80-3.62 (m, 1H), 2.58-2.41 (m, 1H), 2.31-2.13 (m, 2H), 1.98-1.77 (m, 2H), 1.54-1.47 (m, 1H), 1.44 (s, 9H), 1.25 (s, 12H)

ESI-MS m/z 324(MH⁺)

Reference Example 4 (R)-tert-Butyl (3-(4,4,5,5-tetramethyl-1,3,2-dioxaborolan-2-yl)cyclohex-3-en-1-yl)carbamate A product of interest was obtained in accordance with Reference Example 3, with the exception that (1S,3R)-3-aminocyclohexanol was used instead of the (1R,3S)-3-aminocyclohexanol.

$^1$H NMR (CDCl₃) δ: 6.56-6.51 (m, 1H), 4.58-4.41 (m, 1H), 3.80-3.62 (m, 1H), 2.58-2.41 (m, 1H), 2.31-2.13 (m, 2H), 1.98-1.77 (m, 2H), 1.54-1.47 (m, 1H), 1.44 (s, 9H), 1.25 (s, 12H)

ESI-MS m/z 324 (MH⁺)

Reference Example 5 tert-Butyl (3-(4,4,5,5-tetramethyl-1,3,2-dioxaborolan-2-yl)cyclohept-3-en-1-yl)carbamate A product of interest was obtained in accordance with Reference Example 1, with the exception that tert-butyl (3-oxocycloheptyl)carbamate was used instead of the tert-butyl (3-oxocyclohexyl) carbamate.

$^1$H NMR (CDCl₃) δ: 6.91-6.84 (m, 1H), 4.66-4.43 (m, 1H), 3.77-3.58 (m, 1H), 2.52-2.37 (m, 2H), 2.30-2.12 (m, 2H), 2.02-1.90 (m, 1H), 1.61 (br s, 3H), 1.43 (s, 9H), 1.26 (s, 12H)

ESI-MS m/z 338 (MH⁺)

TABLE 1

| | Structural formula |
|---|---|
| Reference Example 1(2a) | *cyclohexenyl-NHBoc with pinacol boronate* |
| Reference Example 1(2b) | *cyclohexenyl-NHBoc with pinacol boronate* |
| Reference Example 2(2a) | *cyclopentenyl-NHBoc with pinacol boronate* |
| Reference Example 2(2b) | *cyclopentenyl-NHBoc with pinacol boronate* |
| Reference Example 3 | *cyclohexenyl-NHBoc (stereochem) with pinacol boronate* |
| Reference Example 4 | *cyclohexenyl-NHBoc (stereochem) with pinacol boronate* |

TABLE 1-continued

Structural formula

Reference Example 5

Example 1 N-(3-(5-phenyl-7H-pyrrolo[2,3-d]pyrimidin-4-yl)cyclohex-3-en-1-yl)acrylamide (Compound 1)

Example 1 (1)tert-Butyl (3-(5-iodo-7-tosyl-7H-pyrrolo[2,3-d]pyrimidin-4-yl)cyclohex-3-en-1-yl)carbamate (Compound 1 (1))

To 4-chloro-7H-pyrrolo[2,3-d]pyrimidin (2.97 g), the compound (9.39 g) of Reference Example 1(2a) and tripotassium phosphate (10.2 g), 1,4-dioxane (66 mL) and water (11 mL) were added, followed by nitrogen substitution, and $PdCl_2(dppf)CH_2Cl_2$ (1.41 g) was then added to the reaction mixture. The thus obtained mixture was stirred at 100° C. for 14 hours. Thereafter, the reaction mixture was cooled to a room temperature, and ethyl acetate and water were then added to the mixture. Thereafter, the thus obtained mixture was filtered through Celite. The filtrate was then extracted with ethyl acetate, and the gathered organic layer was then washed with water and then with a saturated saline. The resultant was dried over anhydrous sodium sulfate, and was then concentrated under a reduced pressure. The obtained residue was purified by silica gel chromatography (chloroform:methanol) to obtain tert-butyl (3-(7H-pyrrolo[2,3-d]pyrimidin-4-yl)cyclohex-3-en-1-yl)carbamate. The above obtained compound was used in the subsequent reaction without further purification.

DMF (100 mL) was added to the obtained compound, and the obtained mixture was then cooled to 0° C. Subsequently, N-iodosuccinimide (6.21 g) was added to the mixture, and the obtained mixture was then stirred at 0° C. for 30 minutes. Thereafter, a 0.5 M sodium hydrogen sulfite aqueous solution was added to the reaction mixture, and the obtained mixture was then extracted with ethyl acetate. The gathered organic layer was washed with water and then with a saturated saline. The resultant was dried over anhydrous sodium sulfate, and was then concentrated under a reduced pressure. The obtained residue was purified by silica gel chromatography (chloroform:methanol) to obtain 3-(5-iodo-7H-pyrrolo[2,3-d]pyrimidin-4-yl)cyclohex-3-en-1-yl)carbamate. The obtained iodine product was subjected to the subsequent reaction without further purification.

DMF (80 mL) was added to the obtained iodine product, and the obtained mixture was then cooled to 0° C. Thereafter, 60% sodium hydride (1.72 g), and then, para-toluenesulfonyl chloride (4.46 g) were added to the reaction mixture, and the obtained mixture was then stirred at 0° C. for 30 minutes. Thereafter, ice water was added to the reaction mixture, and the water layer was then extracted with ethyl acetate. The gathered organic layer was washed with water and then with a saturated saline. The resultant was dried over anhydrous sodium sulfate, and was then concentrated under a reduced pressure. The obtained residue was purified by silica gel chromatography (hexane:ethyl acetate) to obtain a product of interest (7.29 g, yield: 63%).

$^1$H NMR (CDCl$_3$) δ: 8.92 (s, 1H), 8.12 (d, J=8.3 Hz, 2H), 7.89 (s, 1H), 7.34 (d, J=8.3 Hz, 2H), 6.05-5.92 (m, 1H), 4.76-4.60 (m, 1H), 4.14-3.97 (m, 1H), 2.90-2.75 (m, J=15.9 Hz, 1H), 2.41 (s, 3H), 2.49-2.29 (m, 3H), 2.06-1.94 (m, 1H), 1.80-1.64 (m, 1H), 1.44 (s, 9H)

ESI-MS m/z 595 (MH$^+$)

Example 1(2)N-(3-(5-Phenyl-7H-pyrrolo[2,3-d]pyrimidin-4-yl)cyclohex-3-en-1-yl)acrylamide (Compound 1)

To Compound 1 (1) (100 mg), phenylboronic acid (41 mg) and tripotassium phosphate (89.2 mg), 1,4-dioxane (1.8 mL) and water (0.3 mL) were added, followed by nitrogen substitution. Thereafter, $PdCl_2(dppf)CH_2Cl_2$ (12.3 mg) was added to the reaction mixture, and the obtained mixture was then stirred at 100° C. for 2 hours. Thereafter, the reaction mixture was cooled to a room temperature, and ethyl acetate and water were then added to the mixture. Thereafter, the thus obtained mixture was filtered through Celite. The filtrate was extracted with ethyl acetate, and the gathered organic layer was washed with water and then with a saturated saline. The resultant was dried over anhydrous sodium sulfate, and was then concentrated under a reduced pressure.

THF (1.0 mL) and a THF solution (1.0 mL) of 1.0 M tetrabutylammonium fluoride were added to the obtained residue, and the obtained mixture was then stirred at a room temperature for 4 hours. The reaction mixture was concentrated under a reduced pressure, and was then purified by silica gel chromatography (chloroform:methanol) to obtain tert-butyl (3-(5-phenyl-7H-pyrrolo[2,3-d]pyrimidin-4-yl)cyclohex-3-en-1-yl)carbamate. The obtained compound was subjected to the subsequent reaction without further purification.

Methanol (1 mL) and a 1,4-dioxane solution (1 mL) of 4 M hydrochloric acid were added to the obtained compound, and the obtained mixture was then stirred at a room temperature for 30 minutes. Thereafter, the reaction mixture was concentrated under a reduced pressure. The atmosphere was set to a nitrogen atmosphere, dichloromethane (3 mL) and diisopropylethylamine (1 mL) were then added to the reaction mixture, and the obtained mixture was then cooled to 0° C. Thereafter, acryloyl chloride (0.1 mL) was added to the reaction mixture, and the obtained mixture was then stirred for 30 minutes. Thereafter, an ammonia aqueous solution, chloroform and methanol were successively added to the reaction mixture, and the thus obtained mixture was then stirred at a room temperature for 1 hour. Thereafter, the reaction mixture was extracted with chloroform, and the gathered organic layer was washed with a saturated saline, was then dried over anhydrous sodium sulfate, and was then concentrated under a reduced pressure. The obtained residue was purified by silica gel chromatography (chloroform:methanol) to obtain the title compound (34.2 mg, yield: 59%).

$^1$H NMR (CDCl$_3$-CD$_3$OD) δ: 8.77 (s, 1H), 7.43-7.27 (m, 6H), 6.29 (dd, J=1.7, 16.8 Hz, 1H), 6.16 (dd, J=10.2, 16.8 Hz, 1H), 5.63 (dd, J=1.7, 10.2 Hz, 1H), 5.50-5.44 (m, 1H), 4.28-4.17 (m, 1H), 2.69-2.46 (m, 2H), 1.94-1.54 (m, 4H)

ESI-MS m/z 345 (MH$^+$)

Example 2 N-(3-(5-(Thiophen-2-yl)-7H-pyrrolo[2,3-d]pyrimidin-4-yl)cyclohex-3-en-1-yl)acrylamide (Compound 2)

The title compound was obtained in accordance with Example 1(2), with the exception that thiophen-2-ylboronic acid was used instead of the phenylboronic acid.

¹H NMR (DMSO-d6) δ: 12.48-12.41 (m, 1H), 8.74 (s, 1H), 8.11 (d, J=7.7 Hz, 1H), 7.73 (d, J=2.2 Hz, 1H), 7.52 (dd, J=1.1, 5.1 Hz, 1H), 7.10 (dd, J=3.3, 5.1 Hz, 1H), 6.94 (dd, J=1.1, 3.3 Hz, 1H), 6.26 (dd, J=10.1, 17.0 Hz, 1H), 6.10 (dd, J=2.2, 17.0 Hz, 1H), 5.59 (dd, J=2.2, 10.1 Hz, 1H), 5.43-5.39 (m, 1H), 4.02-3.87 (m, 1H), 2.95-2.81 (m, 1H), 2.47-2.36 (m, 1H), 1.98-1.74 (m, 3H), 1.53-1.36 (m, 1H)
ESI-MS m/z 351 (MH⁺)

Example 3 N-(3-(5-(Thiophen-3-yl)-7H-pyrrolo[2,3-d]pyrimidin-4-yl)cyclohex-3-en-1-yl)acrylamide (Compound 3)

The title compound was obtained in accordance with Example 1(2), with the exception that thiophen-3-ylboronic acid was used instead of the phenylboronic acid.
¹H NMR (DMSO-d₅) δ: 12.42-12.14 (m, 1H), 8.72 (s, 1H), 8.10 (d, J=7.3 Hz, 1H), 7.67 (d, J=2.6 Hz, 1H), 7.55 (dd, J=2.9, 5.1 Hz, 1H), 7.33 (dd, J=1.1, 2.9 Hz, 1H), 7.07 (dd, J=1.1, 5.1 Hz, 1H), 6.27 (dd, J=10.3, 16.9 Hz, 1H), 6.10 (dd, J=2.2, 16.9 Hz, 1H), 5.59 (dd, J=2.2, 10.3 Hz, 1H), 5.36-5.31 (m, 1H), 4.02-3.89 (m, 1H), 2.99-2.88 (m, 1H), 2.47-2.40 (m, 1H), 1.91-1.72 (m, 3H), 1.54-1.41 (m, 1H)
ESI-MS m/z 351 (MH⁺)

Example 4 N-(3-(5-(Furan-3-yl)-7H-pyrrolo[2,3-d]pyrimidin-4-yl)cyclohex-3-en-1-yl)acrylamide (Compound 4)

The title compound was obtained in accordance with Example 1(2), with the exception that furan-3-ylboronic acid was used instead of the phenylboronic acid.
¹H NMR (CDCl₃) δ: 8.74 (s, 1H), 7.51-7.49 (m, 1H), 7.48-7.46 (m, 1H), 7.35 (s, 1H), 6.43-6.41 (m, 1H), 6.29 (dd, J=1.7, 17.1 Hz, 1H), 6.19 (dd, J=10.0, 17.1 Hz, 1H), 5.78-5.72 (m, 1H), 5.65 (dd, J=1.7, 10.0 Hz, 1H), 4.33-4.22 (m, 1H), 2.71-2.61 (m, 1H), 2.56-2.45 (m, 1H), 2.18-1.96 (m, 2H), 1.91-1.73 (m, 2H)
ESI-MS m/z 335 (MH⁺)

Example 5 N-(3-(5-(Furan-2-yl)-7H-pyrrolo[2,3-d]pyrimidin-4-yl)cyclohex-3-en-1-yl)acrylamide (Compound 5)

DMF (6.2 mL) was added to Compound 1(1) (740 mg) and tributyl(furan-2-yl)stannane (890 mg), followed by nitrogen substitution. Thereafter, PdCl₂(PPh₃)₂ (87 mg) was added to the reaction mixture, and the obtained mixture was then stirred under heating at 100° C. for 2 hours. Thereafter, a saturated sodium hydrogen carbonate aqueous solution and ethyl acetate were added to the reaction mixture, and the obtained mixture was stirred and was then filtered through Celite. The filtrate was extracted with ethyl acetate, and the gathered organic layer was washed with a saturated saline, was then dried over anhydrous sodium sulfate, and was then concentrated under a reduced pressure.
The obtained residue was dissolved in THF (5 mL), a THF solution (5 mL) of 1.0 M tetrabutylammonium fluoride was then added to the obtained solution. The thus obtained mixture was stirred at a room temperature for 1 hour. Thereafter, a 0.067 M phosphate buffer (pH 7.4) was added to the reaction mixture, and the obtained mixture was then extracted with ethyl acetate. The gathered organic layer was washed with a saturated saline, was then dried over anhydrous sodium sulfate, and was then concentrated under a reduced pressure. The obtained residue was purified by silica gel chromatography (hexane:ethyl acetate) to obtain tert-butyl (3-(5-(furan-2-yl)-7H-pyrrolo[2,3-d]pyrimidin-4-yl)cyclohex-3-en-1-yl)carbamate.

The obtained compound was subjected to the subsequent reaction without further purification.
Methanol (3 mL) and a 1,4-dioxane solution (4 mL) of 4 M hydrochloric acid were added to the obtained coupling product, and the obtained mixture was then stirred at a room temperature for 30 minutes. Thereafter, the reaction mixture was concentrated under a reduced pressure. The atmosphere was set to a nitrogen atmosphere, dichloromethane (6.2 mL) and diisopropylethylamine (2.21 mL) were then added to the reaction mixture, and the obtained mixture was then cooled to 0° C. Thereafter, acryloyl chloride (0.20 mL) was added to the reaction mixture, and the obtained mixture was then stirred for 30 minutes. Thereafter, an ammonia aqueous solution, chloroform and methanol were successively added to the reaction mixture, and the thus obtained mixture was then stirred at a room temperature for 1 hour. Thereafter, the reaction mixture was extracted with chloroform, and the gathered organic layer was washed with a saturated saline, was then dried over anhydrous sodium sulfate, and was then concentrated under a reduced pressure. The obtained residue was purified by silica gel chromatography (chloroform:methanol) to obtain the title compound (348 mg, yield: 840).
¹H NMR (DMSO-d₆) δ: 8.76 (s, 1H), 7.54-7.44 (m, 2H), 6.51-6.12 (m, 4H), 5.73-5.57 (m, 2H), 4.39-4.27 (m, 1H), 2.80-2.68 (m, 1H), 2.56-2.47 (m, 1H), 2.17-1.60 (m, 4H)
ESI-MS m/z 335 (MH⁺)

Example 6 (R)—N-(3-(5-(Furan-2-yl)-7H-pyrrolo[2,3-d]pyrimidin-4-yl)cyclohex-3-en-1-yl)acrylamide (Compound 6)

Example 6(1) (R)-tert-Butyl (3-(5-iodo-7-tosyl-7H-pyrrolo[2,3-d]pyrimidin-4-yl)cyclohex-3-en-1-yl)carbamate (Compound 6(1))

The title compound was obtained in accordance with Example 1(1), with the exception that the compound of Reference Example 4 was used instead of the compound of Reference Example 1(2a).
¹H NMR (CDCl₃) δ: 8.92 (s, 1H), 8.12 (d, J=8.3 Hz, 2H), 8.12 (d, J=8.3 Hz, 2H), 7.89 (s, 1H), 7.34 (d, J=8.0 Hz, 1H), 6.02-5.96 (m, 1H), 4.76-4.63 (m, 1H), 4.12 (s, 1H), 2.90-2.76 (m, 1H), 2.41 (s, 3H), 2.51-2.27 (m, 3H), 2.06-1.95 (m, 1H), 1.81-1.67 (m, 1H), 1.44 (s, 9H)
ESI-MS m/z 595 (MH⁺)

Example 6(2) (R)—N-(3-(5-(Furan-2-yl)-7H-pyrrolo[2,3-d]pyrimidin-4-yl)cyclohex-3-en-1-yl)acrylamide (Compound 6)

The title compound was obtained in accordance with Example 5, with the exception that Compound 6(1) was used instead of Compound 1(1).
¹H NMR (DMSO-d₆) δ: 12.53-12.38 (m, 1H), 8.74 (s, 1H), 8.13 (d, J=7.6 Hz, 1H), 7.79 (d, J=2.7 Hz, 1H), 7.69 (dd, J=0.7, 2.0 Hz, 1H), 6.56 (dd, J=2.0, 3.2 Hz, 1H), 6.39 (dd, J=0.7, 3.2 Hz, 1H), 6.27 (dd, J=10.0, 17.1 Hz, 1H), 6.11 (dd, J=2.4, 17.1 Hz, 1H), 5.59 (dd, J=2.4, 10.0 Hz, 1H), 5.52-5.46 (m, 1H), 4.08-3.93 (m, 1H), 2.94-2.83 (m, 1H), 2.47-2.33 (m, 1H), 2.06-1.96 (m, J=5.9 Hz, 2H), 1.88-1.79 (m, 1H), 1.59-1.43 (m, 1H)
ESI-MS m/z 335 (MH⁺)

Example 7 (S)—N-(3-(5-(Furan-2-yl)-7H-pyrrolo[2,3-d]pyrimidin-4-yl)cyclohex-3-en-1-yl)acrylamide (Compound 7)

Example 7(1) 4-Chloro-5-iodo-7-trityl-7H-pyrrolo[2,3-d]pyrimidine (Compound 7(1))

Trityl chloride (134 g) was added to a chloroform (1 L) solution of 4-chloro-5-iodo-7H-pyrrolo[2,3-d]pyrimidine (111 g) and triethylamine (84 mL) under cooling on ice. The obtained mixture was stirred at a room temperature for 1 hour, and the reaction mixture was then concentrated. Methanol (400 mL) was added to the obtained residue, and thereafter, a solid was collected by filtration, was then washed with methanol, and was then dried to obtain the title compound (204 g, yield: 980).

$^1$H NMR (CDCl$_3$) δ: 8.27 (s, 1H), 7.39 (s, 1H), 7.31-7.28 (m, 9H), 7.15-7.11 (m, 6H).

ESI-MS m/z 522 (MH$^+$)

Example 7(2) 4-Chloro-5-(furan-2-yl)-7-trityl-7H-pyrrolo[2,3-d]pyrimidine (Compound 7(2))

Under a nitrogen atmosphere, a 1,4-dioxane (750 mL) solution of Compound 7(1) (78.3 g) and Pd(PPh$_3$)$_4$ (8.7 g) was heated to 90° C., and thereafter, a 1 M sodium carbonate aqueous solution (180 mL) of 2-furylboronic acid (21.4 g) was added to the reaction solution over 6 hours. The reaction mixture was further stirred at 90° C. for 3 hours, and the reaction solvent was then distilled away under a reduced pressure. Thereafter, water (1 L) was added to the residue, and the obtained mixture was then extracted with ethyl acetate. The gathered organic layer was washed with a saturated saline, was then dried over anhydrous sodium sulfate, and was then concentrated under a reduced pressure. Methanol was added to the obtained residue. A solid was collected by filtration, was then washed with methanol, and was the dried to obtain the title compound (59.8 g, yield: 86%).

$^1$H-NMR (CDCl$_3$) δ: 8.31 (s, 1H), 7.52 (s, 1H), 7.45 (d, J=1.8 Hz, 1H), 7.31-7.28 (m, 9H), 7.19-7.15 (m, 6H), 6.72 (d, J=3.3 Hz, 1H), 6.48 (dd, J=3.3, 1.8 Hz, 1H).

ESI-MS m/z 462 (MH$^+$)

Example 7(3) (S)-tert-Butyl (3-(5-(furan-2-yl)-7-trityl-7H-pyrrolo[2,3-d]pyrimidin-4-yl)cyclohex-3-en-1-yl)carbamate (Compound 7(3))

Under a nitrogen atmosphere, a 1,4-dioxane (150 mL) solution of Compound 7(2) (13.4 g), Pd(PPh$_3$)$_4$ (1.68 g), the compound of Reference Example 3 (10.32 g) and a 2 M sodium carbonate aqueous solution (32 mL) was stirred at 105° C. overnight. Thereafter, the reaction mixture was cooled to a room temperature, and ethyl acetate and water were then added thereto. Thereafter, the obtained mixture was dispensed, and the organic layer was washed with a saturated saline, was then dried over anhydrous sodium sulfate, and was then concentrated under a reduced pressure. The obtained residue was purified by silica gel chromatography (hexane:ethyl acetate) to obtain the title compound (15.69 g, yield: 870).

$^1$H-NMR (CDCl$_3$) δ: 8.52 (s, 1H), 7.53 (s, 1H), 7.36 (s, 1H), 7.32-7.26 (m, 9H), 7.22-7.17 (m, 6H), 6.43 (dd, J=2.9, 1.8 Hz, 1H), 6.29 (d, J=3.3 Hz, 1H), 5.72-5.69 (m, 1H), 4.85 (d, J=8.1 Hz, 1H), 4.04 (s, 1H), 2.98-2.90 (m, 1H), 2.47-2.37 (m, 1H), 2.11-1.94 (m, 2H), 1.86-1.78 (m, 1H), 1.72-1.64 (m, 1H), 1.46 (s, 9H).

ESI-MS m/z 623 (MH$^+$)

Example 7(4) (S)-3-(5-(Furan-2-yl)-7H-pyrrolo[2,3-d]pyrimidin-4-yl)cyclohex-3-senamin (Compound 7(4))

A mixed solution of Compound 7(3) (12.3 g), 2-propanol (120 mL) and a 2 M mesylic acid aqueous solution (50 mL) was stirred at 85° C. for 3 hours. Thereafter, the reaction mixture was cooled to a room temperature, water was then added thereto, and the organic solvent was then distilled away under a reduced pressure. The water layer was washed with ethyl acetate, and the water layer was then converted to a basic layer with 5 M sodium hydroxide. It was then extracted with a chloroform-ethanol (4/1) mixed solvent. The extract was dried over anhydrous sodium sulfate, and was then concentrated under a reduced pressure. The obtained solids were gathered, were then washed with ethyl acetate, and was then dried to obtain the title compound (4.32 g, yield: 78%).

$^1$H-NMR (CD$_3$OD) δ: 8.69 (s, 1H), 7.62 (s, 1H), 7.56 (dd, J=1.8, 0.7 Hz, 1H), 6.49 (dd, J=3.1, 2.0 Hz, 1H), 6.39 (d, J=3.3 Hz, 1H), 5.64-5.61 (m, 1H), 3.11-3.03 (m, 1H), 2.85-2.78 (m, 1H), 2.30-2.21 (m, 1H), 2.11-2.05 (m, 2H), 1.90-1.83 (m, 1H), 1.53-1.43 (m, 1H).

ESI-MS m/z 281 (MH$^+$)

Example 7(5) (S)—N-(3-(5-(Furan-2-yl)-7H-pyrrolo[2,3-d]pyrimidin-4-yl)cyclohex-3-en-1-yl)acrylamide (Compound 7)

An acetonitrile solution (5.17 mL) of 2 M acryloyl chloride was added to a solution of Compound 7(4) (2.76 g), ethanol (100 mL) and diisopropylethylamine (2.01 mL) under cooling on ice over 10 minutes. Thereafter, water was added to the reaction solution, and the organic solvent was then distilled away under a reduced pressure. The precipitated solid was collected by filtration, and was then washed with water and ethyl acetate. The resultant was dried to obtain the title compound (3.03 g, yield: 92%).

$^1$H-NMR (DMSO-d$_6$) δ: 12.46 (s, 1H), 8.73 (s, 1H), 8.12 (d, J=7.3 Hz, 1H), 7.78 (d, J=2.6 Hz, 1H), 7.68 (dd, J=1.8, 0.7 Hz, 1H), 6.55 (dd, J=3.3, 1.8 Hz, 1H), 6.38 (d, J=3.3 Hz, 1H), 6.25 (dd, J=17.2, 9.9 Hz, 1H), 6.09 (dd, J=17.0, 2.4 Hz, 1H), 5.58 (dd, J=10.1, 2.4 Hz, 1H), 5.50-5.47 (m, 1H), 4.04-3.94 (m, 1H), 2.86 (dd, J=16.9, 5.1 Hz, 1H), 2.46-2.38 (m, 1H), 2.02-1.96 (m, 2H), 1.86-1.79 (m, 1H), 1.55-1.44 (m, 1H).

ESI-MS m/z 335 (MH$^+$)

Example 8 N-(3-(5-(Furan-2-yl)-7H-pyrrolo[2,3-d]pyrimidin-4-yl)cyclopent-3-en-1-yl)acrylamide (Compound 8)

Example 8(1) tert-Butyl (3-(5-iodo-7-tosyl-7H-pyrrolo[2,3-d]pyrimidin-4-yl)cyclopent-3-en-1-yl)carbamate (Compound 8 (1))

The title compound was obtained in accordance with Example 1(1), with the exception that the compound of Reference Example 2(2a) was used instead of the compound of Reference Example 1(2a).

$^1$H NMR (CDCl$_3$) δ: 8.94 (s, 1H), 8.12 (d, J=8.3 Hz, 2H), 7.34 (d, J=8.3 Hz, 2H), 7.27 (s, 1H), 6.19-6.14 (m, 1H), 4.97-4.86 (m, 1H), 4.63-4.46 (m, 1H), 3.29-3.19 (m, 1H), 3.15-3.01 (m, 1H), 2.72 (d, J=16.3 Hz, 1H), 2.58-2.48 (m, 1H), 2.41 (s, 3H), 1.45 (s, 9H)

ESI-MS m/z 581 (MH$^+$)

Example 8(2) N-(3-(5-(Furan-2-yl)-7H-pyrrolo[2,3-d]pyrimidin-4-yl)cyclopent-3-en-1-yl)acrylamide (Compound 8)

The title compound was obtained in accordance with Example 5, with the exception that Compound 8(1) was used instead of Compound 1(1).

¹H NMR (CDCl₃) δ: 8.78 (s, 1H), 7.54 (s, 1H), 7.47-7.44 (m, 1H), 6.47 (dd, J=2.0, 3.2 Hz, 1H), 6.34-6.26 (m, 2H), 6.15 (dd, J=10.2, 17.1 Hz, 1H), 5.65 (dd, J=1.6, 10.1 Hz, 1H), 5.63-5.60 (m, 1H), 4.75-4.65 (m, 1H), 3.22-3.08 (m, 1H), 2.87-2.76 (m, 2H), 2.46-2.36 (m, 1H)
ESI-MS m/z 321 (MH⁺)

Example 9 N-(3-(5-Phenyl-7H-pyrrolo[2,3-d]pyrimidin-4-yl)cyclopent-3-en-1-yl)acrylamide (Compound 9)

Example 9 (1) 4-Chloro-5-iodo-7-tosyl-7H-pyrrolo[2,3-d]pyrimidine (Compound 9(1))

DMF (100 mL) was added to 4-chloro-5-iodo-7H-pyrrolo[2,3-d]pyrimidine (10 g), and the obtained mixture was then cooled to 0° C. Thereafter, 601 sodium hydride (2.15 g), and then, p-toluenesulfonyl chloride (8.19 g) were added to the reaction mixture, and the thus obtained mixture was then stirred at 0° C. for 1 hour. After that, ice water was added to the reaction mixture, and the water layer was then extracted with ethyl acetate. The gathered organic layer was washed with water and then with a saturated saline. The resultant was dried over anhydrous sodium sulfate, and was then concentrated under a reduced pressure. The obtained residue was purified by silica gel chromatography (hexane:ethyl acetate) to obtain a product of interest (14.1 g, yield: 911).
¹H NMR (CDCl₃) δ: 8.75 (s, 1H), 8.10 (d, J=8.5 Hz, 2H), 7.95 (s, 1H), 7.35 (d, J=8.5 Hz, 2H), 2.42 (s, 3H))
ESI-MS m/z 434 (MH⁺)

Example 9(2) 4-Chloro-5-phenyl-7-tosyl-7H-pyrrolo[2,3-d]pyrimidine (Compound 9(2))

1,4-Dioxane (18 mL) and water (3 mL) were added to Compound 9(1) (1.71 g), phenylboronic acid (530 mg) and tripotassium phosphate (1.67 g), followed by nitrogen substitution. Thereafter, PdCl₂(dppf)CH₂Cl₂ (280 mg) was added to the reaction mixture, and the obtained mixture was then stirred at 60° C. for 3 hours. Thereafter, the reaction mixture was cooled to a room temperature, ethyl acetate and water were then added thereto, and the obtained mixture was then filtrated through Celite. The filtrate was extracted with ethyl acetate. The gathered organic layer was washed with water, and then with a saturated saline. The resultant was then dried over anhydrous sodium sulfate, and was then concentrated under a reduced pressure. The obtained residue was purified by silica gel chromatography (hexane:ethyl acetate) to obtain a product of interest (1.21 g, 84%).
¹H NMR (CDCl₃) δ: 8.79 (s, 1H), 8.14 (d, J=8.5 Hz, 2H), 7.76 (s, 1H), 7.50-7.41 (m, 5H), 7.36 (d, J=8.5 Hz, 2H), 2.43 (s, 3H)
ESI-MS m/z 384 (MH⁺)

Example 9(3) N-(3-(5-Phenyl-7H-pyrrolo[2,3-d]pyrimidin-4-yl)cyclopent-3-en-1-yl)acrylamide (Compound 9)

1,4-Dioxane (1.8 mL) and water (0.3 mL) were added to Compound 9(2) (125 mg), the compound of Reference Example 2(2a) (127 mg) and tripotassium phosphate (181 mg), followed by nitrogen substitution. Thereafter, PdCl₂(dppf)CH₂Cl₂ (25 mg) was added to the reaction mixture, and the obtained mixture was then stirred at 100° C. for 4 hours. Thereafter, the reaction mixture was cooled to a room temperature, ethyl acetate and water were then added thereto, and the obtained mixture was then filtrated through Celite. The filtrate was extracted with ethyl acetate. The gathered organic layer was washed with water, and then with a saturated saline. The resultant was dried over anhydrous sodium sulfate, and was then concentrated under a reduced pressure.
THF (1 mL) and a THF solution (1 mL) of 1.0 M tetrabutylammonium fluoride were added to the obtained residue, and the obtained mixture was then stirred at a room temperature for 1 hour. The reaction mixture was concentrated under a reduced pressure, and was then purified by silica gel chromatography (chloroform:methanol) to obtain tert-butyl (3-(5-phenyl-7H-pyrrolo[2,3-d]pyrimidin-4-yl)cyclopent-3-en-1-yl)carbamate.
Methanol (2 mL) and a 1,4-dioxane solution (2 mL) of 4 M hydrochloric acid were added to the above obtained compound, and the obtained mixture was then stirred at a room temperature for 30 minutes. Thereafter, the reaction mixture was concentrated under a reduced pressure. The atmosphere was converted to a nitrogen atmosphere, and dichloromethane (3.0 mL) and diisopropylethylamine (1.0 mL) were then added to the reaction mixture. The obtained mixture was cooled to 0° C. Acryloyl chloride (0.1 mL) was added to the reaction mixture, and the obtained mixture was then stirred for 30 minutes. Thereafter, an ammonia aqueous solution, chloroform and methanol were successively added to the reaction mixture, and the thus obtained mixture was then stirred at a room temperature for 1 hour. Subsequently, the reaction mixture was extracted with chloroform, and the gathered organic layer was then washed with a saturated saline. The resultant was dried over anhydrous sodium sulfate, and was then concentrated under a reduced pressure. The obtained residue was purified by silica gel chromatography (chloroform:methanol) to obtain the title compound (74.7 mg, yield: 60%).
¹H NMR (CDCl₃) δ: 8.78 (s, 1H), 7.42-7.23 (m, 6H), 6.30-6.21 (m, 1H), 6.18-6.04 (m, 1H), 5.68-5.59 (m, 1H), 5.41-5.34 (m, 1H), 4.63-4.51 (m, 1H), 3.03-2.92 (m, 1H), 2.81-2.71 (m, 1H), 2.58-2.46 (m, 1H), 2.28-2.17 (m, 1H)
ESI-MS m/z 331 (MH⁺)

Example 10 N-(3-(5-Phenyl-7H-pyrrolo[2,3-d]pyrimidin-4-yl)cyclopent-2-en-1-yl)acrylamide (Compound 10)

The title compound was obtained in accordance with Example 9(3), with the exception that the compound of Reference Example 2(2b) was used instead of the compound of Reference Example 2(2a).
¹H NMR (CDCl₃) δ: 8.79 (s, 1H), 7.59-7.18 (m, 6H), 6.23 (dd, J=1.5, 17.1 Hz, 1H), 6.01 (dd, J=10.5, 17.1 Hz, 1H), 5.65 (dd, J=1.5, 10.5 Hz, 1H), 5.41-5.34 (m, 1H), 4.95-4.75 (m, 1H), 2.87-2.65 (m, 2H), 2.47-2.31 (m, 1H), 1.72-1.57 (m, 1H)
ESI-MS m/z 331 (MH⁺)

Example 11 N-(3-(5-Phenyl-7H-pyrrolo[2,3-d]pyrimidin-4-yl)cyclohept-3-en-1-yl)acrylamide (Compound 11)

The title compound was obtained in accordance with Example 9(3), with the exception that the compound of Reference Example 5 was used instead of the compound of Reference Example 2(2a).
¹H NMR (CDCl₃) δ: 8.75 (s, 1H), 7.44-7.26 (m, 6H), 6.24-6.16 (m, 2H), 5.90-5.82 (m, 1H), 5.65-5.58 (m, 1H), 4.18-4.08 (m, 1H), 2.66-2.59 (m, 2H), 2.14-1.76 (m, 4H), 1.49-1.38 (m, 2H)
ESI-MS m/z 359 (MH⁺)

Example 12 N-(3-(5-Phenyl-7H-pyrrolo[2,3-d]pyrimidin-4-yl)cyclohex-2-en-1-yl)acrylamide (Compound 12)

Example 12(1) tert-Butyl (3-(5-iodo-7-tosyl-7H-pyrrolo[2,3-d]pyrimidin-4-yl)cyclohex-2-en-1-yl)carbamate (Compound 12(1))

1,4-Dioxane (78 mL) and water (13 mL) were added to 4-chloro-7H-pyrrolo[2,3-d]pyrimidine (3.89 g), Reference Example 1(2b) (12.3 g) and tripotassium phosphate (13.4 g), followed by nitrogen substitution. Thereafter, PdCl$_2$(dppf)CH$_2$Cl$_2$ (1.85 g) was added to the reaction mixture, and the obtained mixture was then stirred at 100° C. for 14 hours. Thereafter, the reaction mixture was cooled to a room temperature, ethyl acetate and water were then added thereto, and the obtained mixture was then filtrated through Celite. The filtrate was extracted with ethyl acetate, and the gathered organic layer was washed with water, and then with a saturated saline. The resultant was dried over anhydrous sodium sulfate, and was then concentrated under a reduced pressure. The obtained residue was purified by silica gel chromatography (chloroform:methanol) to obtain tert-butyl (3-(7H-pyrrolo[2,3-d]pyrimidin-4-yl)cyclohex-2-en-1-yl)carbamate.

DMF (50 mL) was added to the above obtained compound, and the obtained mixture was then cooled to 0° C. Thereafter, N-iodosuccinimide (4.03 g) was added to the reaction mixture, and the obtained mixture was then stirred at 0° C. for 30 minutes. Thereafter, a 0.5 M sodium hydrogen sulfite aqueous solution was added to the reaction mixture, and the obtained mixture was then extracted with ethyl acetate. The gathered organic layer was washed with water, and then with a saturated saline. The resultant was dried over anhydrous sodium sulfate, and was then concentrated under a reduced pressure. The obtained residue was purified by silica gel chromatography (chloroform:methanol) to obtain tert-butyl (3-(5-iodo-7H-pyrrolo[2,3-d]pyrimidin-4-yl)cyclohex-2-en-1-yl)carbamate.

DMF (50 mL) was added to the obtained iodine product, and the obtained mixture was then cooled to 0° C. After that, 60% sodium hydride (1.01 g), and then p-toluenesulfonyl chloride (2.63 g) were added to the reaction mixture, and the thus obtained mixture was then stirred at 0° C. for 30 minutes. Thereafter, ice water was added to the reaction mixture, and the water layer was then extracted with ethyl acetate. The gathered organic layer was washed with water, and then with a saturated saline. The resultant was dried over anhydrous sodium sulfate, and was then concentrated under a reduced pressure. The obtained residue was purified by silica gel chromatography (hexane:ethyl acetate) to obtain a product of interest (2.41 g, yield: 16%).

$^1$H NMR (CDCl$_3$) δ: 8.94 (s, 1H), 8.12 (d, J=8.3 Hz, 2H), 7.90 (s, 1H), 7.34 (d, J=8.3 Hz, 2H), 5.88-5.79 (m, 1H), 4.78-4.64 (m, 1H), 4.54-4.36 (m, 1H), 2.58-2.28 (m, 5H), 2.11-1.97 (m, 1H), 1.89 (br. s., 2H), 1.77-1.64 (m, 1H), 1.43 (s, 9H)

ESI-MS m/z 595 (MH$^+$)

Example 12(2) N-(3-(5-Phenyl-7H-pyrrolo[2,3-d]pyrimidin-4-yl)cyclohex-2-en-1-yl)acrylamide (Compound 12)

1,4-Dioxane (1.8 mL) and water (0.3 mL) were added to Compound 12(1) (30 mg), phenylboronic acid (10 mg) and tripotassium phosphate (32 mg), followed by nitrogen substitution. Thereafter, PdCl$_2$(dppf)CH$_2$Cl$_2$ (7.4 mg) was added to the reaction mixture, and the obtained mixture was then stirred at 100° C. for 2 hours. Thereafter, the reaction mixture was cooled to a room temperature, ethyl acetate and water were then added thereto, and the obtained mixture was then filtrated through Celite. The filtrate was extracted with ethyl acetate, and the gathered organic layer was washed with water, and then with a saturated saline. The resultant was dried over anhydrous sodium sulfate, and was then concentrated under a reduced pressure.

THF (1.0 mL) and a THF solution (1.0 mL) of 1.0 M tetrabutylammonium fluoride were added to the obtained residue, and the obtained mixture was then stirred at a room temperature 4 hours. Thereafter, the reaction mixture was concentrated under a reduced pressure, and was then purified by silica gel chromatography (chloroform:methanol) to obtain tert-butyl (3-(5-phenyl-7H-pyrrolo[2,3-d]pyrimidin-4-yl)cyclohex-2-en-1-yl)carbamate.

Methanol (1 mL) and a 1,4-dioxane solution (1 mL) of 4 M hydrochloric acid were added to the above obtained compound, and the obtained mixture was then stirred at a room temperature for 30 minutes. Thereafter, the reaction mixture was then concentrated under a reduced pressure. The atmosphere was converted to a nitrogen atmosphere, and dichloromethane (1 mL) and diisopropylethylamine (0.1 mL) were then added to the reaction mixture. The thus obtained mixture was cooled to 0° C. Acryloyl chloride (0.012 mL) was added to the reaction mixture, and the obtained mixture was then stirred for 30 minutes. Thereafter, an ammonia aqueous solution, chloroform and methanol were successively added to the reaction mixture, and the obtained mixture was then stirred at a room temperature for 1 hour. Thereafter, the reaction mixture was extracted with chloroform. The gathered organic layer was washed with a saturated saline, was then dried over anhydrous sodium sulfate, and was then concentrated under a reduced pressure. The obtained residue was purified by silica gel chromatography (chloroform:methanol) to obtain the title compound (18 mg).

$^1$H NMR (CDCl$_3$) δ: 8.81 (s, 1H), 7.50-7.28 (m, 6H), 6.22 (dd, J=1.2, 17.0 Hz, 1H), 5.92 (dd, J=10.4, 17.0 Hz, 1H), 5.63 (dd, J=1.3, 10.4 Hz, 1H), 5.36-5.26 (m, 1H), 4.41-4.30 (m, 1H), 2.74-2.56 (m, 1H), 2.46-2.27 (m, 1H), 1.98-1.32 (m, 4H)

ESI-MS m/z 345 (MH$^+$)

Example 13 N-(3-(5-(Thiophen-2-yl)-7H-pyrrolo[2,3-d]pyrimidin-4-yl)cyclohex-2-en-1-yl)acrylamide (Compound 13)

The title compound was obtained in accordance with Example 12(2), with the exception that thiophen-2-ylboronic acid was used instead of the phenylboronic acid.

$^1$H NMR (CDCl$_3$) δ: 8.83-8.53 (m, 1H), 7.47-6.76 (m, 4H), 6.28-5.84 (m, 2H), 5.68-5.28 (m, 2H), 4.46-4.16 (m, 1H), 2.58-2.11 (m, 2H), 1.93-1.26 (m, 4H)

ESI-MS m/z 351 (MH$^+$)

Example 14 N-(3-(5-(Thiophen-3-yl)-7H-pyrrolo[2,3-d]pyrimidin-4-yl)cyclohex-2-en-1-yl)acrylamide (Compound 14)

The title compound was obtained in accordance with Example 12(2), with the exception that thiophen-3-ylboronic acid was used instead of the phenylboronic acid.

$^1$H NMR (CDCl$_3$) δ: 8.76 (s, 1H), 7.43 (dd, J=2.9, 4.9 Hz, 1H), 7.40 (d, J=6.6 Hz, 1H), 7.24-7.22 (m, 1H), 7.08 (dd, J=1.0, 4.9 Hz, 1H), 6.28-6.21 (m, 1H), 6.15-6.06 (m, 1H), 5.68-5.62 (m, 1H), 5.53-5.48 (m, 1H), 4.46-4.34 (m, 1H), 2.52-2.24 (m, 2H), 2.05-1.39 (m, 4H)
ESI-MS m/z 351 (MH$^+$)

Example 15 N-(3-(5-(Furan-2-yl)-7H-pyrrolo[2,3-d]pyrimidin-4-yl)cyclohex-2-en-1-yl)acrylamide (Compound 15)

The title compound was obtained in accordance with Example 5, with the exception that Compound 12(1) was used instead of Compound 1(1).
$^1$H NMR (CDCl$_3$) δ: 8.78 (s, 1H), 7.54 (dd, J=0.7, 1.9 Hz, 1H), 7.52 (s, 1H), 6.55 (dd, J=1.9, 2.9 Hz, 1H), 6.39 (dd, J=0.7, 2.9 Hz, 1H), 6.25 (dd, J=1.6, 17.0 Hz, 1H), 6.09 (dd, J=10.5, 17.1 Hz, 1H), 5.64 (dd, J=1.5, 10.2 Hz, 1H), 5.57-5.53 (m, 1H), 4.57-4.46 (m, 1H), 2.54-2.40 (m, 2H), 2.03-1.72 (m, 3H), 1.67-1.52 (m, 1H)
ESI-MS m/z 335 (MH$^+$)

Example 16 N-(3-(5-(Furan-3-yl)-7H-pyrrolo[2,3-d]pyrimidin-4-yl)cyclohex-2-en-1-yl)acrylamide (Compound 16)

The title compound was obtained in accordance with Example 9, with the exceptions that furan-3-ylboronic acid was used instead of the phenylboronic acid, and that the compound of Reference Example 1(2b) was used instead of the compound of Reference Example 2(2a).
ESI-MS m/z 335(MH$^+$)

Comparative Example 1 N-(3-(5-Phenyl-7H-pyrrolo[2,3-d]pyrimidin-4-yl)cyclohex-3-en-1-yl)methacrylamide The title compound was obtained in accordance with Example 1(2), with the exception that methacryloyl chloride was used instead of the acryloyl chloride.
$^1$H NMR (CDCl$_3$) δ: 8.76 (s, 1H), 7.46-7.21 (m, 6H), 5.73-5.64 (m, 1H), 5.49-5.40 (m, 1H), 5.38-5.32 (m, 1H), 4.29-4.11 (m, 1H), 2.79-2.45 (m, 2H), 2.01-1.93 (m, 3H), 1.92-1.77 (m, 1H), 1.76-1.55 (m, 3H)
ESI-MS m/z 359 (MH$^+$)

Comparative Example 2 (E)-N-(3-(5-Phenyl-7H-pyrrolo[2,3-d]pyrimidin-4-yl)cyclohex-3-en-1-yl)but-2-enamide Methanol (1 mL) and a 1,4-dioxane solution (1 mL) of 4 M hydrochloric acid were added to the tert-butyl (3-(5-phenyl-7H-pyrrolo[2,3-d]pyrimidin-4-yl)cyclohex-3-en-1-yl)carbamate (50 mg) obtained in Example 1(2), and the obtained mixture was then stirred at a room temperature for 30 minutes. Thereafter, the reaction mixture was concentrated under a reduced pressure. The atmosphere was converted to a nitrogen atmosphere, and dichloromethane (2 mL) and diisopropylethylamine (0.2 mL) were then added to the reaction mixture. The thus obtained mixture was then cooled to 0° C. After that, (E)-but-2-enoyl chloride (0.02 mL) was added to the reaction mixture, and the obtained mixture was then stirred for 30 minutes. Thereafter, an ammonia aqueous solution, chloroform and methanol were successively added to the reaction mixture. The thus obtained mixture was stirred at a room temperature for 1 hour. Thereafter, the reaction mixture was extracted with chloroform, and the gathered organic layer was then washed with a saturated saline. The resultant was dried over anhydrous sodium sulfate, and was then concentrated under a reduced pressure. The obtained residue was purified by silica gel chromatography (chloroform:methanol) to obtain the title compound (41.1 mg, yield: 90%).
$^1$H NMR (CDCl$_3$) δ: 8.82-8.70 (m, 1H), 7.50-7.21 (m, 6H), 6.95-6.70 (m, 1H), 5.94-5.79 (m, 1H), 5.53-5.39 (m, 1H), 4.30-4.07 (m, 1H), 2.75-2.41 (m, 2H), 1.97-1.53 (m, 7H)
ESI-MS m/z 359 (MH$^+$)

Comparative Example 3 N-(3-(5-(3-Cyanophenyl)-7H-pyrrolo[2,3-d]pyrimidin-4-yl)cyclohex-3-en-1-yl)acrylamide The title compound was obtained in accordance with Example 1(2), with the exception that (3-cyanophenyl)boronic acid was used instead of the phenylboronic acid.
$^1$H NMR (CDCl$_3$) δ: 8.80 (s, 1H), 7.70-7.43 (m, 5H), 6.34-6.09 (m, 2H), 5.65 (d, J=10.0 Hz, 1H), 5.51-5.38 (m, 1H), 4.35-4.14 (m, 1H), 2.82-2.66 (m, 1H), 2.62-2.47 (m, 1H), 2.01-1.59 (m, 4H)
ESI-MS m/z 370 (MH$^+$)

Comparative Example 4 N-(3-(5-(p-Tolyl)-7H-pyrrolo[2,3-d]pyrimidin-4-yl)cyclohex-3-en-1-yl)acrylamide The title compound was obtained in accordance with Example 1(2), with the exception that p-tolylboronic acid was used instead of the phenylboronic acid.
$^1$H NMR (CDCl$_3$) δ: 8.75 (s, 1H), 7.36 (s, 1H), 7.25-7.12 (m, 4H), 6.29 (dd, J=1.9, 17.1 Hz, 1H), 6.17 (dd, J=10.2, 17.1 Hz, 1H), 5.64 (dd, J=1.9, 10.2 Hz, 1H), 5.49 (br. S., 1H), 4.27-4.09 (m, 1H), 2.67-2.43 (m, 2H), 2.40 (s, 3H), 1.99-1.50 (m, 4H)
ESI-MS m/z 359 (MH$^+$)

Comparative Example 5 N-(3-(5-(3-Fluorophenyl)-7H-pyrrolo[2,3-d]pyrimidin-4-yl)cyclohex-3-en-1-yl)acrylamide The title compound was obtained in accordance with Example 1(2), with the exception that (3-fluorophenyl)boronic acid was used instead of the phenylboronic acid.
$^1$H NMR (CDCl$_3$) δ: 8.77 (s, 1H), 7.44 (s, 1H), 7.44-7.35 (m, 1H), 7.17-6.98 (m, 3H), 6.34-6.15 (m, 2H), 5.70-5.63 (m, 1H), 5.56-5.48 (m, 1H), 4.28-4.16 (m, 1H), 2.77-2.46 (m, 2H), 2.02-1.61 (m, 4H)
ESI-MS m/z 363 (MH$^+$)

Comparative Example 6 N-(3-(5-(Pyridin-3-yl)-7H-pyrrolo[2,3-d]pyrimidin-4-yl)cyclohex-3-en-1-yl)acrylamide The title compound was obtained in accordance with Example 1(2), with the exception that 3-(4,4,5,5-tetramethyl-1,3,2-dioxaborolan-2-yl)pyridine was used instead of the phenylboronic acid.
$^1$H NMR (CDCl$_3$) δ: 8.81 (s, 1H), 8.54-8.49 (m, 2H), 7.72-7.67 (m, 1H), 7.48 (s, 1H), 7.43-7.39 (m, 1H), 6.31 (dd, J=2.2, 17.1 Hz, 1H), 6.23 (dd, J=9.5, 17.1 Hz, 1H), 5.65 (dd, J=2.2, 9.5 Hz, 1H), 5.42-5.36 (m, 1H), 4.33-4.23 (m, 1H), 2.89-2.78 (m, 1H), 2.57-2.47 (m, 1H), 1.86-1.65 (m, 4H)
ESI-MS m/z 346 (MH$^+$)

Comparative Example 7 N-(3-(5-(1-Methyl-1H-pyrazol-4-yl)-7H-pyrrolo[2,3-d]pyrimidin-4-yl)cyclohex-3-en-1-yl)acrylamide The title compound was obtained in accordance with Example 1(2), with the exception that 1-methyl-4-(4,4,5,5- tetramethyl-1,3,2-dioxaborolan-2-yl)-1H-pyrazole was used instead of the phenylboronic acid.

$^1$H NMR (DMSO-d$_6$) δ: 12.23-12.19 (m, 1H), 8.69 (s, 1H), 8.10 (d, J=7.3 Hz, 1H), 7.62 (s, 1H), 7.55 (d, J=2.6 Hz, 1H), 7.37 (s, 1H), 6.27 (dd, J=9.9, 16.9 Hz, 1H), 6.11 (dd, J=2.2, 16.9 Hz, 1H), 5.59 (dd, J=2.2, 9.9 Hz, 1H), 5.44-5.36 (m, 1H), 4.04-3.92 (m, 1H), 3.87 (s, 3H), 2.94-2.83 (m, 1H), 2.47-2.38 (m, 1H), 2.05-1.78 (m, 3H), 1.59-1.43 (m, 1H)

ESI-MS m/z 349 (MH$^+$)

Comparative Example 8 N-(3-(5-(Pyrimidin-2-yl)-7H-pyrrolo[2,3-d]pyrimidin-4-yl)cyclohex-3-en-1-yl)acrylamide The title compound was obtained in accordance with Example 5, with the exception that 2-(tributylstannyl)pyrimidine was used instead of the tributyl(furan-2-yl)stannane.

$^1$H NMR (CDCl$_3$) δ: 8.82 (s, 1H), 8.82 (d, J=5.1 Hz, 2H), 8.04 (s, 1H), 7.26 (t, J=5.1 Hz, 1H), 6.31 (dd, J=2.2, 17.1 Hz, 1H), 6.22 (dd, J=9.8, 17.1 Hz, 1H), 5.66 (dd, J=2.2, 9.8 Hz, 1H), 5.53-5.47 (m, 1H), 4.41-4.32 (m, 1H), 3.02-2.93 (m, 1H), 2.65-2.55 (m, 1H), 2.09-1.77 (m, 4H)

ESI-MS m/z 347 (MH$^+$)

Comparative Example 9 N-(3-(5-(Benzofuran-2-yl)-7H-pyrrolo[2,3-d]pyrimidin-4-yl)cyclohex-3-en-1-yl)acrylamide The title compound was obtained in accordance with Example 1(2), with the exception that benzofuran-2-ylboronic acid was used instead of the phenylboronic acid.

$^1$H NMR (CDCl$_3$) δ: 8.81 (s, 1H), 7.73 (s, 1H), 7.63-7.55 (m, 1H), 7.51 (d, J=8.1 Hz, 1H), 7.38-7.22 (m, 2H), 7.19 (d, J=7.3 Hz, 1H), 6.74 (s, 1H), 6.31 (dd, J=1.6, 17.0 Hz, 1H), 6.16 (dd, J=10.1, 17.0 Hz, 1H), 5.79-5.75 (m, 1H), 5.64 (dd, J=1.6, 10.1 Hz, 1H), 4.41-4.32 (m, 1H), 2.92-2.82 (m, 1H), 2.66-2.54 (m, 1H), 2.02-1.91 (m, 1H), 1.89-1.61 (m, 3H)

ESI-MS m/z 385 (MH$^+$)

Comparative Example 10 4-(Cyclohex-1-en-1-yl)-7H-pyrrolo[2,3-d]pyrimidine 1,4-Dioxane (2.0 mL) and water (0.3 mL) were added to 4-chloro-7H-pyrrolo[2,3-d]pyrimidine (30 mg), 2-(cyclohex-1-en-1-yl)-4,4,5,5-tetramethyl-1,3,2-dioxaborolane (48.8 mg) and tripotassium phosphate (124 mg), followed by nitrogen substitution. Thereafter, PdCl$_2$(dppf)CH$_2$Cl$_2$ (28.5 mg) was added to the reaction mixture, and the obtained mixture was then stirred at 100° C. for 14 hours. Thereafter, the reaction mixture was cooled to a room temperature, ethyl acetate and water were then added thereto, and the obtained mixture was then filtrated through Celite. The filtrate was extracted with ethyl acetate, and the gathered organic layer was washed with water, and then with a saturated saline. The resultant was dried over anhydrous sodium sulfate, and was then concentrated under a reduced pressure. The obtained residue was purified by silica gel chromatography (hexane: ethyl acetate) to obtain a product of interest (15 mg, yield: 38%).

$^1$H NMR (CDCl$_3$) δ: 9.90-9.64 (m, 1H), 8.83 (s, 1H), 7.31 (dd, J=2.4, 3.7 Hz, 1H), 6.91-6.85 (m, 1H), 6.74 (dd, J=2.0, 3.7 Hz, 1H), 2.80-2.64 (m, 2H), 2.43-2.27 (m, 2H), 1.93-1.71 (m, 4H)

ESI-MS m/z 200 (MH$^+$)

Comparative Example 11

Comparative Example 11(1a)

tert-Butyl ((1S,3R)-3-(5-(furan-2-yl)-7H-pyrrolo[2,3-d]pyrimidin-4-yl)cyclohexyl)carbamate Comparative Example 11(1b)

tert-Butyl ((1S,3S)-3-(5-(furan-2-yl)-7H-pyrrolo[2,3-d]pyrimidin-4-yl)cyclohexyl)carbamate 1,4-Dioxane (72 mL) and water (12 mL) were added to 4-chloro-7H-pyrrolo[2,3-d]pyrimidine (2.0 g), the compound of Reference Example 3 (5.1 g) and tripotassium phosphate (6.9 g), followed by nitrogen substitution. Thereafter, PdCl$_2$(dppf)CH$_2$Cl$_2$ (1.4 g) was added to the reaction mixture, and the obtained mixture was then stirred at 100° C. for 14 hours. Thereafter, the reaction mixture was cooled to a room temperature, chloroform and water were then added thereto, and the obtained mixture was then filtrated through Celite. The filtrate was extracted with chloroform, and the gathered organic layer was washed with water, and then with a saturated saline. The resultant was dried over anhydrous sodium sulfate, and was then concentrated under a reduced pressure. The obtained residue was purified by silica gel chromatography (hexane:acetone) to obtain the corresponding coupling product. The obtained coupling product was used in the subsequent reaction without further purification.

THF (200 mL) and a 10% palladium carbon catalyst (2.0 g) were added to the obtained coupling product. The atmosphere was converted to a hydrogen atmosphere, and the mixture was then stirred at a room temperature for 14 hours. Thereafter, the reaction mixture was filtrated through Celite, and was then washed with THF. After that, the filtrate was concentrated under a reduced pressure. The obtained residue was purified by silica gel chromatography (hexane:acetone) to obtain the corresponding coupling product (3.12 g, yield: 76%).

ESI-MS m/z 317(MH$^+$)

DMF (30 mL) was added to the obtained coupling product (3.04 g), and the obtained mixture was then cooled to 0° C. After that, N-iodosuccinimide (2.59 g) was added to the reaction mixture, and the obtained mixture was then stirred at 0° C. for 30 minutes. Thereafter, a 0.5 M sodium hydrogen sulfite aqueous solution was added to the reaction mixture, and the obtained mixture was then extracted with ethyl acetate. The gathered organic layer was washed with water, and then with a saturated saline. The resultant was dried over anhydrous sodium sulfate, and was then concentrated under a reduced pressure. The obtained residue was purified by silica gel chromatography (hexane:acetone) to obtain the corresponding iodine product. The obtained iodine product was used in the subsequent reaction without further purification.

DMF (36 mL) was added to the obtained iodine product, and the obtained mixture was then cooled to 0° C., After that, 60% sodium hydride (0.72 g), and then, p-toluenesulfonyl chloride (1.86 g) were added to the reaction mixture, and the thus obtained mixture was then stirred at 0° C. for 30 minutes. Thereafter, ice water was added to the reaction mixture, and the water layer was then extracted with ethyl acetate. The gathered organic layer was washed with water, and then with a saturated saline. The resultant was dried over anhydrous sodium sulfate, and was then concentrated under a reduced pressure. The obtained residue was purified by silica gel chromatography (hexane:ethyl acetate) to obtain the corresponding tosyl product (4.22 g, yield: 74%).

ESI-MS m/z 597(MH$^+$)

DMF (42 mL) was added to the tosyl product (4.20 g) and tributyl(furan-2-yl)stannane (5.03 g), followed by nitrogen substitution. Thereafter, PdCl$_2$(PPh$_3$)$_2$ (494 mg) was added to the reaction mixture, and the obtained mixture was then stirred under heating at 100° C. for 30 minutes. Thereafter, a saturated sodium hydrogen carbonate aqueous solution and ethyl acetate were added to the reaction mixture, and the thus obtained mixture was stirred and was then filtrated through Celite. The filtrate was extracted with ethyl acetate. The gathered organic layer was washed with a saturated saline, was then dried over anhydrous sodium sulfate, and was then concentrated under a reduced pressure. The obtained residue was purified by silica gel chromatography (hexane:ethyl acetate) to obtain the compound of Comparative Example 11(1a) (1.71 g, yield: 45%) and the compound of Comparative Example 11(1b) (1.99 g, yield: 53%), respectively.

Comparative Example 11(1a) $^1$H NMR (CDCl$_3$) δ: 8.94 (s, 1H), 8.13 (d, J=8.3 Hz, 2H), 7.80 (s, 1H), 7.63 (s, 1H), 7.34 (d, J=8.3 Hz, 2H), 6.55-6.51 (m, 2H), 4.43 (d, J=7.6 Hz, 1H), 3.55-3.37 (m, 1H), 3.09 (tt, J=3.2, 11.7 Hz, 1H), 2.41 (s, 3H), 2.15-1.94 (m, 2H), 1.88-1.53 (m, 3H), 1.42 (s, 9H), 1.50-1.20 (m, 2H), 1.18-1.02 (m, 1H)

ESI-MS m/z 537 (MH$^+$)

Comparative Example 11(1b) $^1$H NMR (CDCl$_3$) δ: 8.96 (s, 1H), 8.15 (d, J=8.3 Hz, 2H), 7.81 (s, 1H), 7.70 (s, 1H), 7.35 (d, J=8.3 Hz, 2H), 6.61-6.54 (m, 2H), 4.57 (d, J=6.3 Hz, 1H), 4.06-3.90 (m, 1H), 3.25-3.03 (m, 1H), 2.42 (s, 3H), 1.99-1.88 (m, 1H), 1.47 (s, 9H), 1.88-1.39 (m, 7H)

ESI-MS m/z 537 (MH$^+$)

Comparative Example 11(a) N-((1S,3R)-3-(5-(Furan-2-yl)-7H-pyrrolo[2,3-d]pyrimidin-4-yl)cyclohexyl)acrylamide The compound of Comparative Example 11(1a) (1.70 g) was dissolved in THF (8.5 mL), and a THF solution (6.3 mL) of 1.0 M tetrabutylammonium fluoride was then added to the solution. The obtained mixture was stirred at a room temperature for 1 hour. Thereafter, a 0.067 M phosphate buffer (pH 7.4) was added to the reaction mixture, and the mixture was then extracted with ethyl acetate. The gathered organic layer was washed with a saturated saline, was then dried over anhydrous sodium sulfate, and was then concentrated under a reduced pressure. The obtained residue was purified by silica gel chromatography (hexane:acetone) to obtain the corresponding detosylated product. The obtained detosylated product was used in the subsequent reaction without further purification.

Methanol (10 mL) and a 1,4-dioxane solution (10 mL) of 4 M hydrochloric acid were added to the obtained detosylated product, and the obtained mixture was then stirred at a room temperature for 40 minutes. Thereafter, the reaction mixture was concentrated under a reduced pressure. The atmosphere was converted to a nitrogen atmosphere, and dichloromethane (20 mL) and diisopropylethylamine (5.28 mL) were then added to the reaction mixture. After that, the mixture was cooled to 0° C. Acryloyl chloride (0.49 mL) was added to the mixture, and the obtained mixture was then stirred for 30 minutes. Thereafter, an ammonia aqueous solution, chloroform and methanol were successively added to the reaction mixture, and the thus obtained mixture was then stirred at a room temperature for 1 hour. Thereafter, the reaction mixture was extracted with chloroform. The gathered organic layer was washed with a saturated saline, was then dried over anhydrous sodium sulfate, and was then concentrated under a reduced pressure. The obtained residue was purified by silica gel chromatography (chloroform:methanol) to obtain the title compound (657 mg, yield: 62%).

$^1$H NMR (DMSO-d$_6$) δ: 12.38 (br s, 1H), 8.71 (s, 1H), 8.07 (d, J=7.8 Hz, 1H), 7.84 (dd, J=0.7, 1.8 Hz, 1H), 7.74 (d, J=2.7 Hz, 1H), 6.62 (dd, J=1.8, 3.3 Hz, 1H), 6.58 (dd, J=0.7, 3.3 Hz, 1H), 6.18 (dd, J=10.0, 16.8 Hz, 1H), 6.06 (dd, J=2.4, 16.8 Hz, 1H), 5.55 (dd, J=2.4, 10.0 Hz, 1H), 3.75-3.56 (m, 1H), 3.24-3.10 (m, 1H), 2.02-1.62 (m, 5H), 1.47 (dt, J=9.4, 12.3 Hz, 1H), 1.34-1.06 (m, 2H)

ESI-MS m/z 337 (MH$^+$)

Comparative Example 11(b) N-((1S,3S)-3-(5-(Furan-2-yl)-7H-pyrrolo[2,3-d]pyrimidin-4-yl)cyclohexyl)acrylamide The title compound was obtained in accordance with Comparative Example 11(a), with the exception that the compound of Comparative Example 11(1b) was used instead of the compound of Comparative Example 11(1a).

$^1$H NMR (DMSO-d$_6$) δ: 12.39 (br s, 1H), 8.72 (s, 1H), 7.78 (d, J=6.1 Hz, 1H), 7.72 (d, J=2.4 Hz, 1H), 7.70 (dd, J=0.7, 1.8 Hz, 1H), 6.54 (dd, J=1.8, 3.2 Hz, 1H), 6.52 (dd, J=0.7, 3.2 Hz, 1H), 6.35 (dd, J=10.1, 17.1 Hz, 1H), 6.04 (dd, J=2.3, 17.1 Hz, 1H), 5.56 (dd, J=2.3, 10.1 Hz, 1H), 4.19-4.03 (m, 1H), 3.76-3.56 (m, 1H), 2.03-1.85 (m, 2H), 1.73-1.46 (m, 6H)

ESI-MS m/z 337 (MH$^+$)

Comparative Example 12 N-(3-(5-Phenyl-7H-pyrrolo[2,3-d]pyrimidin-4-yl)phenyl)acrylamide The title compound was obtained according to the method described in International Publication No. WO 2013/085802.

ESI-MS m/z 341 (MH$^+$)

TABLE 2

| Compound No. | Structural formula |
|---|---|
| 1 | |
| 2 | |

TABLE 2-continued

| Compound No. | Structural formula |
|---|---|
| 3 | |
| 4 | |
| 5 | |
| 6 | |
| 7 | |
| 8 | |
| 9 | |
| 10 | |
| 11 | |
| 12 | |
| 13 | |

TABLE 2-continued
| Compound No. | Structural formula |
|---|---|
| 14 | 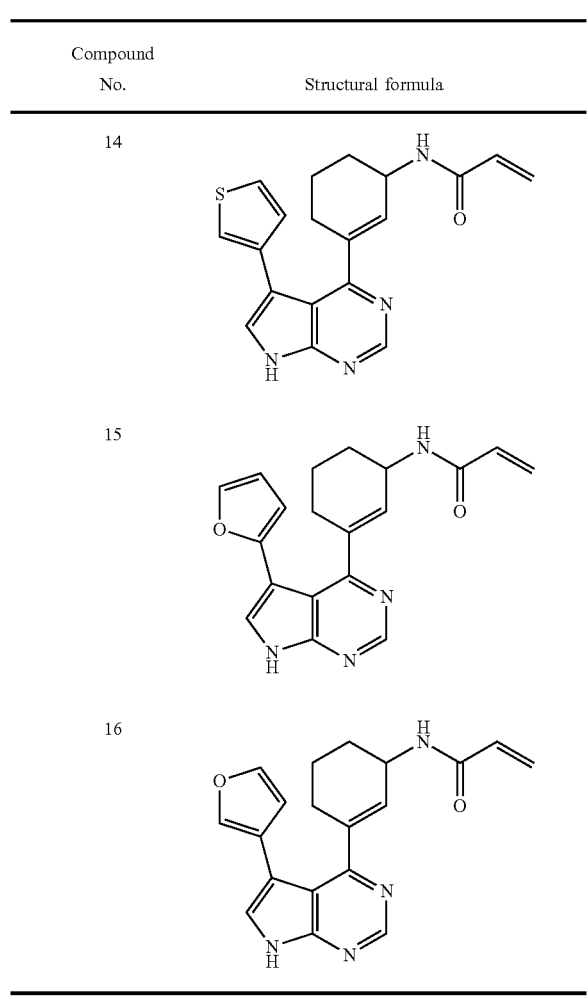 |
| 15 | |
| 16 | |
TABLE 3
| Compound No. | Structural formula |
|---|---|
| Comparative Example 1 | 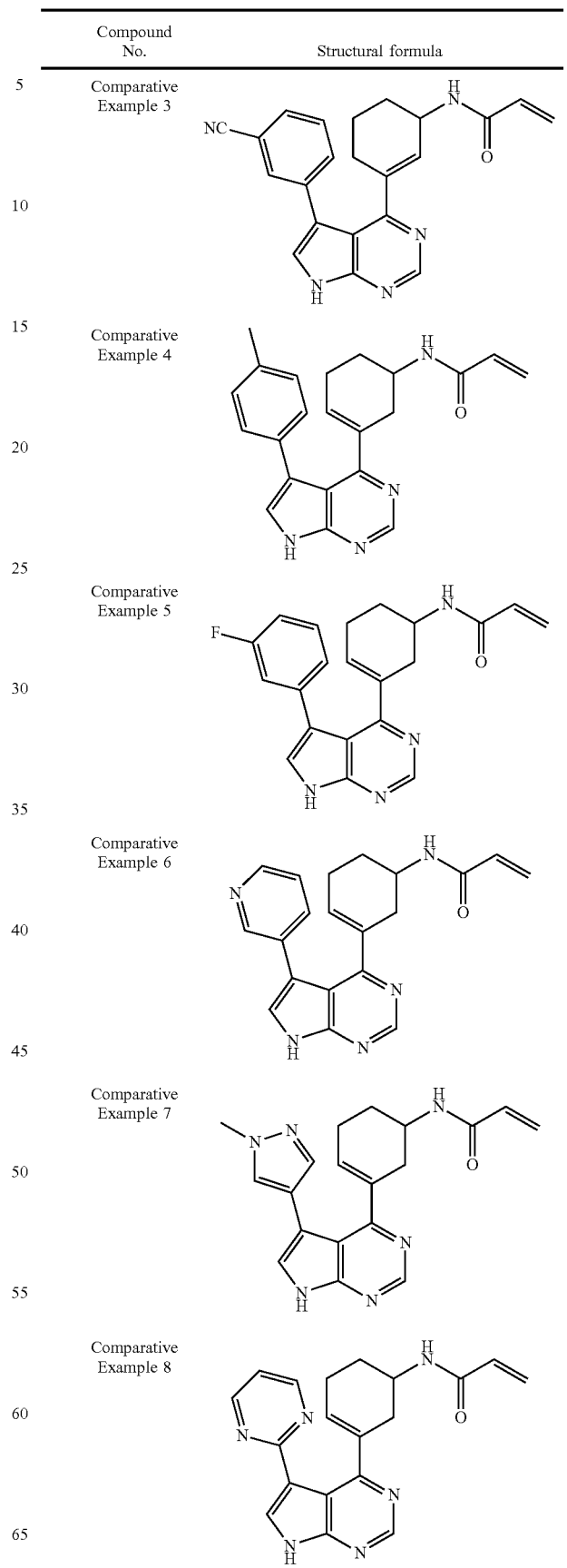 |
| Comparative Example 2 | |
| Comparative Example 3 | |
| Comparative Example 4 | |
| Comparative Example 5 | |
| Comparative Example 6 | |
| Comparative Example 7 | |
| Comparative Example 8 | |

TABLE 3-continued

| Compound No. | Structural formula |
|---|---|
| Comparative Example 9 | 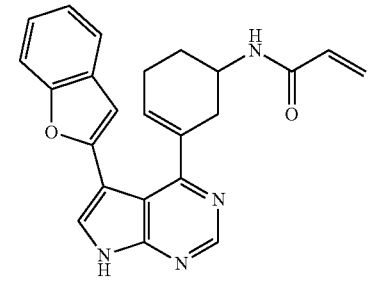 [SMILES: C=CC(=O)NC1CCC=C(c2ncnc3[nH]cc(-c4cc5ccccc5o4)c23)C1] |
| Comparative Example 10 | 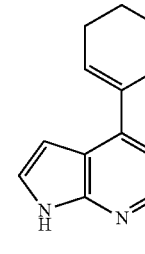 |
| Comparative Example 11(a) | 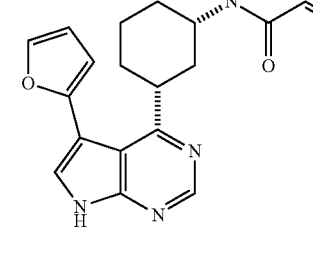 |
| Comparative Example 11(b) | 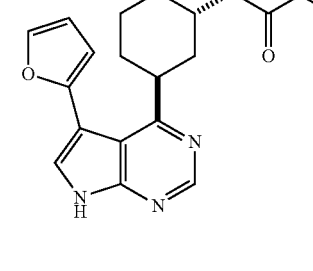 |
| Comparative Example 12 | 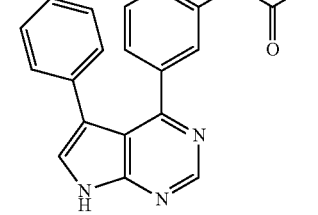 |

TEST EXAMPLES

The compound according to the present invention was evaluated by the following test methods.

Test Example 1 Test Regarding Action to Inhibit Various JAK Kinase Activities (In Vitro)

1) Measurement of JAK1 Kinase-Inhibiting Activity

The activity of the compound of the present invention to inhibit the activity of JAK1 kinase was measured.

Among materials for the measurement of this inhibiting activity, a substrate peptide and a kinase protein were acquired as follows. As such a substrate peptide, a substrate peptide for QSS Assist JAK1-MSA assay kit (Carna Biosciences, Inc.) was purchased. As such a kinase protein, a purified recombinant human JAK1 protein (Carna Biosciences, Inc.) was purchased.

The method for measuring the inhibiting activity is as follows. First, the compounds of the present invention were each dissolved in dimethyl sulfoxide (DMSO), and a serial dilution was then prepared using DMSO. Subsequently, a serial dilution solution of the compound (the final concentration of DMSO upon a kinase reaction: 5.0%) or DMSO (final concentration: 5.0%) was mixed with a solution comprising the substrate peptide (final concentration: 1 μM), magnesium chloride (final concentration: 5 mM) and ATP (final concentration: 75 μM) in a buffer for kinase reaction (20 mM HEPES (pH 7.5), 2 mM dithiothreitol and 0.01% Triton X-100). Thereafter, a JAK1 protein was further added to the mixed solution, and the obtained mixture was then incubated at 25° C. for 120 minutes to carry out a kinase reaction. To the reaction solution, EDTA was added to a final concentration of 30 mM, so as to terminate the reaction. Finally, using LabChip EZ Reader II (Perkin Elmer Corp.), an unphosphorylated substrate peptide (S) and a phosphorylated peptide (P) were subjected to microchannel capillary electrophoresis, so that the two peptides were separated from each other and were then detected. The amount of a phosphorylation reaction was obtained based on the heights of the peaks of S and P, and the concentration of the compound capable of inhibiting 50% of the phosphorylation reaction was defined as an $IC_{50}$ value (nM). The obtained data are shown in a table below.

2) Measurement of JAK2 Kinase-Inhibiting Activity

The activity of the compound of the present invention to inhibit the activity of JAK2 kinase was measured.

Among materials for the measurement of this inhibiting activity, a substrate peptide and a kinase protein were acquired as follows. As such a substrate peptide, FL-Peptide 22 (Perkin Elmer Corp.) was purchased. As such a kinase protein, a purified recombinant human JAK2 protein (Carna Biosciences, Inc.) was purchased.

The method for measuring the inhibiting activity is as follows. First, a serial dilution of the compound of the present invention was prepared by the same method as that described in the above section regarding JAK1. This serial dilution solution (the final concentration of DMSO upon a kinase reaction: 5.0%) or DMSO (final concentration: 5.0%) was mixed with a solution comprising the substrate peptide (final concentration: 1 μM), magnesium chloride (final concentration: 10 mM) and ATP (final concentration: 10 μM) in a buffer for kinase reaction (15 mM Tris (pH 7.5), 2 mM dithiothreitol and 0.01% Tween 20). Thereafter, a JAK2 protein was further added to the mixed solution, and the obtained mixture was then incubated at 25° C. for 80 minutes to carry out a kinase reaction. To the reaction solution, EDTA was added to a final concentration of 30 mM, so as to terminate the reaction. After termination of the reaction, the measurement and the data analysis were carried out by the same methods as those described in the above section regarding JAK1.

3) Measurement of JAK3 Kinase-Inhibiting Activity

The activity of the compound of the present invention to inhibit the activity of JAK3 kinase was measured.

Among materials for the measurement of this inhibiting activity, a substrate peptide and a kinase protein were acquired as follows. As such a substrate peptide, a substrate peptide for QSS Assist JAK3-MSA assay kit (Carna Biosciences, Inc.) was purchased. As such a kinase protein, a purified recombinant human JAK3 protein (Carna Biosciences, Inc.) was purchased.

The method for measuring the inhibiting activity is as follows. First, a serial dilution of the compound of the present invention was prepared by the same method as that described in the above section regarding JAK1. This serial dilution solution (the final concentration of DMSO upon a kinase reaction: 5.0%) or DMSO (final concentration: 5.0%) was mixed with a solution comprising the substrate peptide (final concentration: 1 µM), magnesium chloride (final concentration: 5 mM) and ATP (final concentration: 5 µM) in a buffer for kinase reaction (20 mM HEPES (pH 7.5), 2 mM dithiothreitol and 0.01% Triton X-100). Thereafter, a JAK3 protein was further added to the mixed solution, and the obtained mixture was then incubated at 25° C. for 80 minutes to carry out a kinase reaction. To the reaction solution, EDTA was added to a final concentration of 30 mM, so as to terminate the reaction. After termination of the reaction, the measurement and the data analysis were carried out by the same methods as those described in the above section regarding JAK1.

The results are shown in the following table.

TABLE 4

| Example No. | JAK1 IC$_{50}$ (nM) | JAK2 IC$_{50}$ (nM) | JAK3 IC$_{50}$ (nM) |
|---|---|---|---|
| 1 | 880 | 470 | <0.30 |
| 2 | 900 | 480 | <0.30 |
| 3 | 1500 | 850 | <0.30 |
| 4 | 2900 | 1300 | 0.42 |
| 5 | 720 | 430 | <0.30 |
| 7 | 440 | 330 | <0.30 |
| 8 | 1400 | 430 | <0.30 |
| 9 | 2100 | 880 | <0.30 |
| 10 | NT | 660 | 0.68 |
| 12 | 3200 | 870 | 0.35 |
| 13 | 3200 | 490 | <0.30 |
| 14 | 5600 | 1200 | <0.30 |
| 15 | 2600 | 450 | 0.33 |
| 16 | 4900 | 1000 | 0.77 |
| Comparative Example 1 | 880 | 1100 | 44 |
| Comparative Example 2 | 730 | 600 | 27 |
| Comparative Example 8 | NT | >10000 | 21.36 |
| Comparative Example 10 | 414 | 166 | 125 |
| Comparative Example 11(a) | >10000 | 2440 | 21 |
| Comparative Example 11(b) | >10000 | 880 | 19 |
| Comparative Example 12 | >1000 | >1000 | 0.09 |

From the aforementioned results, it was found that the compound of the present invention exhibited an extremely strong JAK3-inhibiting activity, and that it had selectivity to JAK3, which was 100 times or more higher than selectivity to JAK1 or JAK2, in terms of IC$_{50}$ value. In contrast, the compounds of Comparative Examples 1, 2 and 8 exhibited a JAK3-inhibiting activity, which was 20 times or more attenuated in comparison to the compound of the present invention. Similarly, the compound of Comparative Example 10 also exhibited a JAK3-inhibiting activity, which was 100 times or more attenuated in comparison to that of the present compound, and the selectivity of the compound of Comparative Example 10 to JAK1 or JAK2 was not observed.

Test Example 2 Test Regarding Growth of Human Peripheral Blood Mononuclear Cells (PBMC)

The activity of the compound of the present invention to inhibit the IL-2-dependent growth reaction of human PBMC, which is caused by JAK3, was measured (Arthritis Rheum. 2010; 62(8): 2283-93).

Using a medium comprising 10 µg/mL PHA-M (Sigma) (which is RPMI-1640 (Sigma) comprising 10% human serum type AB (MP Biomedicals)), human PBMC (C.T.L.) (cell density: 1×10$^6$ cells/mL) was cultured at 37° C. in a culture vessel comprising 5% carbon dioxide for 3 days. Thereafter, the culture was washed with RPMI-1640 four times, and a medium (RPMI-1640 comprising 10% human serum type AB) was then added to the resultant culture to prepare a cell suspension. The cells (1×10$^4$ cells per well) and the serially diluted compound of the present invention were added to each well of a 96-well U-bottom microplate, and the thus obtained mixture was then cultured at 37° C. in a culture vessel comprising 5% carbon dioxide for 30 minutes. After completion of the culture, recombinant human IL-2 (Peprotech) was added to the culture to a final concentration of 2 ng/mL, and the obtained mixture was then stirred at 37° C. in a culture vessel comprising 5% carbon dioxide for 2 days (1×10$^4$ cells/100 µl/each well). After completion of the culture, the resultant was left at a room temperature for 30 minutes, and 100 µl of CellTiter-Glo Luminescent Cell Viability Assay (Promega) was then added to the resultant, followed by stirring it. Thereafter, the reaction mixture was left for 10 minutes, and the amount of a luminescence derived from living cells in each well was then measured using a microplate reader (TECAN). The inhibition rate of the present compound to the cell growth caused by IL-2 stimulation was calculated, and the concentration of the compound capable of inhibiting 50% of the cell growth was defined as an IC$_{50}$ value (nM). The obtained data are shown in a table below.

TABLE 5

| Compound No. | PBMC IC$_{50}$ (nM) |
|---|---|
| 2 | 110 |
| 5 | 38 |
| 7 | 18 |
| 8 | 83 |
| 9 | 99 |
| 13 | 110 |
| 14 | 110 |
| Comparative Example 3 | >1000 |
| Comparative Example 4 | >1000 |
| Comparative Example 9 | >1000 |
| Comparative Example 11(a) | >3000 |
| Comparative Example 11(b) | 1942 |
| Comparative Example 12 | 546 |

From the aforementioned results, it was found that the compound of the present invention exhibited an extremely strong growth inhibiting activity, having an IC$_{50}$ value regarding suppression of the growth of human PBMC, which was approximately 100 nM or less. In contrast, the IC$_{50}$ values of the compounds of the comparative examples were attenuated (1000 nM or more).

Test Example 3 Evaluation of Oral Absorbability

The compound of the present invention was suspended or dissolved in 0.1 N HCl and 0.5% HPMC aqueous solution, and then, the obtained suspension or solution was orally administered to BALB/cA mice. Blood was collected from the fundus, 0.5, 1, 2, 4 and 6 hours after completion of the oral administration, and plasma was then obtained from the collected blood. The concentration of the compound in the obtained plasma was measured by LCMS, and the value of area under the blood concentration-time curve (AUC) was then obtained. As a result, the compound of the present invention exhibited good oral absorbability.

Test Example 4 Mouse IL-2-Induced IFN-γ Production Test

The inhibitory activity of the compound of the present invention and the compounds of comparative examples on mouse IL-2-induced IFN-γ production caused by JAK3 was measured (Arthritis Rheum. 2010; 62 (8): 2283-93, Inflammation Research 2015; 64 (1): 41-51).

Seven-week-old male BALB/c mice (Charles River Japan) were divided into five groups (6 mice per group), namely, a vehicle group, a Compound 7 (1 mpk) group, a Compound 7 (3 mpk) group, a Comparative Example 12 (1 mpk) group, and a Comparative Example 12 (3 mpk) group. Compound 7 and the compound of Comparative Example 12 were each administered to the 1 mpk group and the 3 mpk group via oral administration at doses of 1 mg/kg and 3 mg/kg, respectively. Thirty minutes later, a mixed solution of an IFN-γ-capturing antibody (BD Biosciences, 10 μg/mouse) and recombinant human IL-2 (Peprotech, 10 μg/mouse) was intraperitoneally administered in a volume of 200 μL to the vehicle group, the Compound 7 (1 mpk) group, the Compound 7 (3 mpk) group, the Comparative Example 12 (1 mpk) group, and the Comparative Example 12 (3 mpk) group. Three hours after administration of IL-2, blood was collected from all of the five groups, and the IFN-γ concentration in the serum was measured using BD In Vivo Capture Assay for Mouse IFN-γ (BD Biosciences). The relative amount of IFN-γ generated by IL-2 stimulation was calculated according to the following calculation formula:

Relative amount of IFN-γ=(IFN-γ concentration of each group)×100/(IFN-γ concentration of vehicle group), and the results are shown in FIG. 1 (mean value±standard error: regarding vs Vehicle, Dunnett test, *: p<0.05, ***: p<0.001; regarding vs Comparative Example 12 (3 mpk), Student t-test, ##: p<0.01).

From the aforementioned results, the compound of the present invention exhibited statistically significantly suppression of IFN-γ production in vivo. On the other hand, the compound of Comparative Example 12 did not exhibit such a significant IFN-γ production-suppressing action as observed in the compound of the present invention.

Test Example 5 Therapeutic Effect on Rheumatoid Arthritis

Collagen-induced arthritis, which is a mouse experimental model for rheumatoid arthritis, was used. The clinical symptoms of arthritis were scored, and using the obtained scores as indicators, the action of the compound of the present invention by oral administration was confirmed. Seven-week-old male DBA/1 mice (Charles River Laboratories Japan, Inc.) were administered with a 10 μL/body solution (emulsion), which had been obtained by mixing a 4 mg/mL bovine type 2 collagen solution (Collagen Research Center) with a Freund's complete adjuvant (DIFCO) in equal amounts, via dorsal intradermal injection (initial immunization). Twenty-one days after the initial immunization, the mice were administered with a 10 μL/body solution (emulsion), which had been obtained by mixing a 4 mg/mL bovine type 2 collagen solution (Collagen Research Center) with a Freund's incomplete adjuvant (DIFCO) in equal amounts, via intradermal injection to the tail base thereof (booster), so as to induce an arthritis reaction (Arthritis Rheum 2010; 62 (8): 2283-93). The compound of the present invention and Tofacitinib were continuously administered to the mice at a dose of 50 mg/kg (50 mpk), twice a day, via oral administration, for 15 days from 8 days after the implementation day of the booster (which is defined as Day 0), whereas Prednisolone was continuously administered to the mice at a dose of 0.3 mg/kg (3 mpk), once a day, via oral administration, for 15 days from 8 days after the implementation day of the booster. On Day 8, Day 11, Day 14, Day 17 and Day 22, the clinical symptoms of arthritis were scored by observation with naked eyes, and the action of the compound of the present invention was then confirmed. The clinical symptoms for each limb were scored (0: not changed, 1: one finger swelled, 2: two or more fingers swelled, 3: instep swelled, 4: all fingers swelled and also wrist or ankle swelled), and a total score from the four limbs was defined as a score for an individual mouse (the highest score: 16).

As a result, it was found that the compound of the present invention showed an excellent therapeutic effect on rheumatoid arthritis.

The mean value of clinical symptom scores (a total of four limbs) was calculated according to the following calculation formula:

Mean value of clinical symptom scores (total of four limbs)=mean value of clinical symptom scores of right forelimb+mean value of clinical symptom scores of left forelimb+mean value of clinical symptom scores of right hindlimb+mean value of clinical symptom scores of left hindlimb. The results are shown in FIG. 2.

Test Example 6 Therapeutic Effect on Multiple Sclerosis

Experimental autoimmune encephalomyelitis, which is a mouse experimental model for multiple sclerosis, was used. Eight-week-old male SJL/J mice (Charles River Laboratories Japan, Inc.) were administered with a mixed solution (emulsion), which had been obtained by mixing a normal saline aqueous solution (1 mg/mL) of a peptide (Toray Research Center, Inc.) corresponding to 139-151 residues of a proteolipid protein with a Freund's complete adjuvant (DIFCO) comprising 4 mg/mL killed *Mycobacterium tuberculosis* (H37Ra) in equal amounts, via intradermal injection in an amount of 100 μL each into two sites of the dorsal portion of each mouse, so as to induce encephalomyelitis. Seven days after the implementation day of the immunization (which is defined as Day 0), the compound of the present invention was continuously administered to the mice for 4 weeks via oral administration of twice a day. On Day 0, Day 2, Day 5, and Days 7 to 35, the clinical symptoms of encephalomyelitis were observed with naked eyes, and the action of the compound of the present invention was then confirmed. The observed clinical symptoms were scored (0: no symptoms, 1: weakened tail, 1.5: complete ptosis of tail, 2: ataxia, 3: light paralysis of hindlimbs, 3.5: paralysis of hindlimbs, 4. complete paralysis of hindlimbs, 4.5: paralysis of four limbs, dying, 5: death).

As a result, it was found that the compound of the present invention showed an excellent therapeutic effect on multiple sclerosis.

The invention claimed is:

1. A compound represented by formula (I), or a salt thereof:

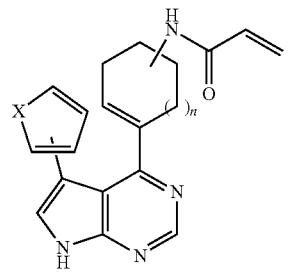

(I)

wherein X represents —CH=CH—, —NH—, a sulfur atom or an oxygen atom; and n represents an integer of 0 to 2.

2. The compound or salt thereof according to claim 1, wherein X is —CH=CH—, a sulfur atom or an oxygen atom, and n is 0 or 1.

3. The compound or salt thereof according to claim 1, wherein, in the formula (I), the structure

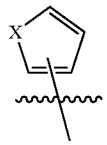

is any one of the structures:

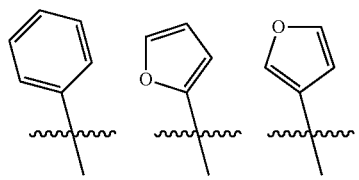

and in the formula (I), the structure

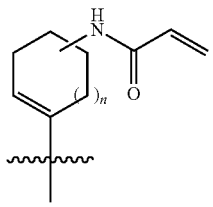

is any one of the structures:

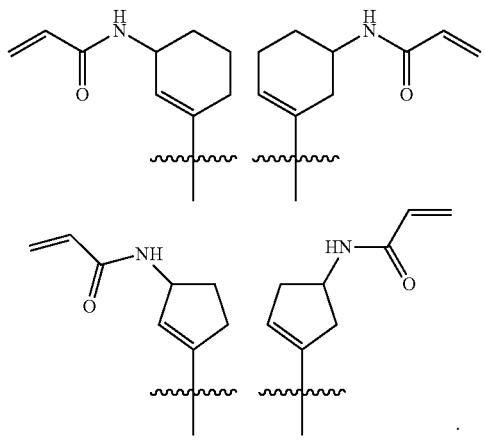

4. The compound or salt thereof according to claim 1, wherein the compound is N-(3-(5-(furan-2-yl)-7H-pyrrolo[2,3-d]pyrimidin-4-yl)cyclohex-3-en-1-yl)acrylamide or (S)—N-(3-(5-(furan-2-yl)-7H-pyrrolo[2,3-d]pyrimidin-4-yl)cyclohex-3-en-1-yl)acrylamide.

5. A JAK3 inhibitor comprising, as an active ingredient, the compound or salt thereof according to claim 1.

6. A pharmaceutical composition comprising the compound or salt thereof according to claim 1, and a pharmaceutically acceptable carrier.

7. A method for inhibiting JAK3, comprising administering an effective amount of the compound or salt thereof according to claim 1 to a subject in need thereof.

8. A method for alleviating one or more symptoms of rheumatoid arthritis or multiple sclerosis, comprising administering an effective amount of the compound or salt thereof according to claim 1 to a subject in need thereof.

* * * * *